(12) United States Patent
Karato et al.

(10) Patent No.: US 7,700,693 B2
(45) Date of Patent: Apr. 20, 2010

(54) CONJUGATED DIENE RUBBER COMPOSTION, PROCESS FOR PRODUCING THE SAME AND RUBBER VULCANIZATE

(75) Inventors: Takeshi Karato, Tokyo (JP); Masao Nakamura, Tokyo (JP); Koichi Endo, Tokyo (JP)

(73) Assignee: Zeon Corporation, Tokyo (JP)

( * ) Notice: Subject to any disclaimer, the term of this patent is extended or adjusted under 35 U.S.C. 154(b) by 806 days.

(21) Appl. No.: 10/570,025

(22) PCT Filed: Sep. 1, 2004

(86) PCT No.: PCT/JP2004/012660

§ 371 (c)(1), (2), (4) Date: Mar. 1, 2006

(87) PCT Pub. No.: WO2005/021637

PCT Pub. Date: Mar. 10, 2005

(65) Prior Publication Data

US 2008/0275184 A1    Nov. 6, 2008

(30) Foreign Application Priority Data

Sep. 1, 2003    (JP) .............................. 2003-308391

(51) Int. Cl.
 *C08L 9/00* (2006.01)
 *C08L 27/10* (2006.01)
 *C08L 43/00* (2006.01)
(52) U.S. Cl. ...................... 525/209; 525/232
(58) Field of Classification Search ................. 525/209, 525/232
See application file for complete search history.

(56) References Cited

U.S. PATENT DOCUMENTS

| 4,657,965 | A | * | 4/1987 | Watanabe et al. | ........... 524/506 |
| 5,652,310 | A | | 7/1997 | Hsu et al. | |
| 5,929,149 | A | | 7/1999 | Matsuo et al. | |
| 6,071,995 | A | | 6/2000 | Labauze | |
| 6,767,969 | B2 | * | 7/2004 | Sasagawa et al. | ........... 525/338 |

FOREIGN PATENT DOCUMENTS

| EP | 0 849 333 A1 | 6/1998 |
| GB | 1 486 807 | 9/1974 |
| JP | H09-110904 A | 4/1997 |
| JP | 2000-273177 A | 10/2000 |
| JP | 2002-80534 A | 3/2002 |

\* cited by examiner

*Primary Examiner*—Nathan M Nutter
(74) *Attorney, Agent, or Firm*—Birch, Stewart, Kolasch & Birch, LLP

(57) ABSTRACT

A conjugated diene rubber composition comprising (A) 5-95 wt. % of a conjugated diene rubber having a structure such that at least three conjugated diene polymer chains are bonded together through a specific polyorganosiloxane having groups containing alkylene glycol repeating units and (B) 95-5 wt. % of a conjugated diene rubber having reacted with a compound having in the molecule a functional group selected from >C=O, >C=S, amino, imino, epoxy, pyridyl, alkoxyl and halogeno. This rubber composition gives, when silica is incorporated therein, a vulcanizable rubber composition having good processability and giving a rubber vulcanizate exhibiting sufficiently reduced heat build up, and having good wet-grip property and good abrasion resistance.

13 Claims, No Drawings

CONJUGATED DIENE RUBBER COMPOSTION, PROCESS FOR PRODUCING THE SAME AND RUBBER VULCANIZATE

TECHNICAL FIELD

This invention relates to a conjugated diene rubber composition, a process for producing the conjugated diene rubber, and a rubber vulcanizate. More specifically this invention relates to a conjugated diene rubber composition characterized as, when it is incorporated with silica, being a vulcanizable rubber composition having good processability and giving a vulcanizate exhibiting reduced heat build up and having enhanced wet-gripping property and high abrasion resistance; and a process for producing the conjugated diene rubber composition; and a rubber vulcanizate made by crosslinking the conjugated diene rubber composition.

BACKGROUND ART

In recent years, vehicle tires having a low fuel consumption are eagerly desired from the viewpoint of protection of environment and conservation of natural resources. Further, good wet-grip property and high abrasion resistance are required for the tires from a viewpoint of safety and durability, respectively.

A silica-incorporated rubber composition exhibits reduced heat build up as compared with the conventional rubber composition having carbon black incorporated therein. Therefore, a silica-incorporated rubber composition is suitable for the production of tires with a low fuel consumption.

Silica generally has a poor affinity for most conventional rubbers. Therefore most rubbers having silica incorporated therein exhibit poor processability and are not satisfactory in heat build up and abrasion resistance. To obviate this problem, a silane coupling agent is often used in combination with silica. However, a silane coupling agent improves the abrasion resistance sometimes only to a very minor extent as compared with the incorporation of carbon black. Further a silane coupling agent is expensive and the incorporation thereof in a sufficient amount is costly.

Attempts of modifying a rubber to enhance its affinity for silica have been made. For example, a silica-incorporated rubber composition is proposed in Japanese Unexamined Patent Publication No. H10-7702 which is made by a diene polymer rubber is lithiated with an organic lithium compound and then the lithiated diene polymer rubber is allowed to react with s silicon-containing compound. A rubber composition comprising a diene polymer containing a silanol group, and a specific carbon black having silica fixed on the surface thereof is proposed in Japanese Unexamined Patent Publication No. H10-316800. The above-proposed rubber compositions give a rubber vulcanizate exhibiting good reduced heat build up, but, the silica-incorporated unvulcanized rubber composition has poor processability and the rubber vulcanizate tends to exhibit poor balance between wet-grip property and abrasion resistance.

A rubber composition comprising a polyorganosiloxane-modified diene polymer rubber and silica is proposed in Japanese Unexamined Patent Publication No. H9-110904. The polyorganosiloxane-modified diene polymer rubber is made by allowing a diene polymer having an active alkali metal terminal, which is prepared by polymerization using an alkali metal polymerization initiator, to react with 0.1 to 2 moles, per mole of the alkali metal polymerization initiator, of a polyorganosiloxane having a specific functional group.

A rubber composition comprising a silsesquioxane-modified diene polymer rubber and silica is proposed in Japanese Unexamined Patent Publication No. 2002-80534. The silsesquioxane-modified diene polymer rubber is made by allowing a diene polymer having an active alkali metal terminal, which is prepared by polymerization using an alkali metal polymerization initiator, to react with 0.1 to 1.5 moles, per mole of the alkali metal polymerization initiator, of a silsesquioxane compound having a polyhedron structure.

The above-proposed polyorganosiloxane-modified diene polymer rubber and the silsesquioxane-modified diene polymer rubber give a rubber vulcanizate having well balanced reduced heat build up and wet-grip property, but, its unvulcanized silica-incorporated rubber composition has poor processability and the rubber vulcaniate tends to have poor abrasion resistance.

Further in the case when a rubber is loaded with carbon black in combination with silica to impart an antistatic property, an abrasion resistance and driving controllability as tire, balance between reduced heat buildup and wet-grip property is not enhanced to the desired extent.

Problems to be Solved by the Invention

In view of the foregoing background art, an object of the present invention is to provide a conjugated diene rubber composition which gives, when silica is incorporated therein, a vulcanizable rubber composition having improved processability and giving a rubber vulcanizate having well reduced heat build up, enhanced wet-grip property and high abrasion resistance; a process for producing the conjugated diene rubber composition; and a rubber vulcanizate.

Means for Solving the Problems

The present inventors made an intensive research for achieving the above-mentioned problems, and found that, when silica is incorporated in a rubber composition comprising specific amounts of (A) a branched conjugated diene rubber having a structure such that at least three conjugated diene polymer chains are bonded together through a polyorganosiloxane, and (B) a conjugated diene rubber having reacted therewith a compound having a specific functional group in the molecule, a resulting vulcanizable rubber composition has improved processability and gives a rubber vulcanizate having well reduced heat build up, good wet-grip property and high abrasion resistance. Based on this finding, the present invention has been completed.

Thus, in one aspect of the present invention, there is provided a conjugated diene rubber composition comprising:

(A) 5% to 95% by weight of a conjugated diene rubber having a weight average molecular weight in the range of 1,000 to 3,000,000 and having a structure such that at least three conjugated diene polymer chains are bonded together through at least one polyorganosiloxane selected from those which are represented by the general formulae (1), (2) and (3), shown below; and (B) 95% to 5% by weight of a conjugated diene rubber having a weight average molecular weight in the range of 1,000 to 3,000,000 and having a structure such that it has been allowed to react with a compound having in the molecule at least one functional group selected from the group consisting of a >C=O group, a >C=S group, an amino group, an imino group, an epoxy group, a pyridyl group, an alkoxyl group and a halogen;

General formula (1):

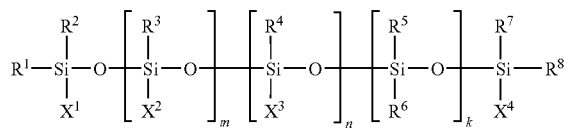

wherein $R^1$ through $R^8$ represent an alkyl group having 1 to 6 carbon atoms or an aryl group having 6 to 12 carbon atoms, $R^1$ through $R^8$ being the same or different; $X^1$ and $X^4$ are such that (i) a part of the sum of $X^1$ and $X^4$ is a functional group capable of reacting with an active metal at a terminal of the active conjugated diene polymer chains and the remainder of the $X^1$ and $X^4$ is a group derived from said functional group or a single bond, or (ii) $X^1$ and $X^4$ are an alkyl group having 1 to 6 carbon atoms or an aryl group having 6 to 12 carbon atoms, $X^1$ and $X^4$ being the same or different; $X^2$ is such that a part of $X^2$ is a functional group capable of reacting with an active metal at a terminal of the active conjugated diene polymer chains and the remainder of $X^2$ is a group derived from said functional group or a single bond; $X^3$ is a group comprising 2 to 20 alkylene glycol repeating units, provided that a part of $X^3$ may be a group derived from the group comprising 2 to 20 alkylene glycol repeating units; and m is an integer of 3 to 200, n is an integer of 0 to 200 and k is an integer of 0 to 200;

General formula (2):

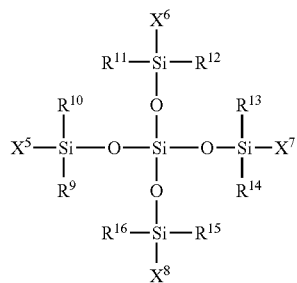

wherein $R^9$ through $R^{16}$ represent an alkyl group having 1 to 6 carbon atoms or an aryl group having 6 to 12 carbon atoms, $R^9$ through $R^{16}$ being the same or different; and $X^5$ through $X^8$ are such that a part of the sum of $X^5$ through $X^8$ is a functional group capable of reacting with an active metal at a terminal of the active conjugated diene polymer chains and the remainder of the sum of $X^5$ through $X^8$ is a group derived from said functional group or a single bond;

General formula (3):

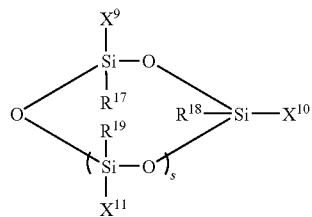

wherein $R^{17}$, $R^{18}$ and $R^{19}$ represent an alkyl group having 1 to 6 carbon atoms or an aryl group having 6 to 12 carbon atoms, $R^{17}$, $R^{18}$ and $R^{19}$ being the same or different; $X^9$, $X^{10}$ and $X^{11}$ are such that a part of the sum of $X^9$, $X^{10}$ and $X^{11}$ is a functional group capable of reacting with an active metal at a terminal of the active conjugated diene polymer chains and the remainder of the sum of $X^1$ and $X^4$ is a group derived from said functional group or a single bond; and s is an integer of 1 to 18.

The polyorganosiloxanes represented by the above-recited formulae (1), (2) and (3) wherein $X^1$ through $X^{11}$ are as defined above are hereinafter referred to as "polyorganosiloxanes after reaction" when appropriate.

In other aspects of the present invention, there are provided the following processes (I) and (II) for producing the above-mentioned conjugated diene polymer rubber.

Production Process (I):

A process for producing the above-mentioned conjugated diene rubber composition, which comprises:

allowing active conjugated diene polymer chains having an active metal at a terminal thereof, which are obtained by polymerizing a conjugated diene monomer alone or both of a conjugated diene monomer and an aromatic vinyl monomer using an organic active metal in an inert solvent, to react with a polyorganosiloxane having a functional group capable of reacting with the active metal at a terminal of the active conjugated diene polymers to prepare a polymer solution of the conjugated diene rubber (A) having a weight average molecular weight in the range of 1,000 to 3,000,000; wherein the amount of said polyorganosiloxane is larger than 0.001 mole but smaller than 0.1 mole, per mole of the organic active metal used for polymerization; and said polyorganosiloxane is at least one polyorganosiloxane selected from those which are represented by the formulae (1), (2) and (3), wherein $X^1$ and $X^4$ in the formula (1) are a functional group capable of reacting with an active metal at a terminal of the active conjugated diene polymer chains, or are an alkyl group having 1 to 6 carbon atoms or an aryl group having 6 to 12 carbon atoms, $X^2$ is a functional group capable of reacting with an active metal at a terminal of the active conjugated diene polymer chains, $X^3$ is a group comprising 2 to 20 alkylene glycol repeating units; and $X^5$ through $X^8$ in the formula (2) are a functional group capable of reacting with an active metal at a terminal of the active conjugated diene polymer chains; and $X^9$ through $X^{11}$ in the formula (3) are a functional group capable of reacting with an active metal at a terminal of the active conjugated diene polymer chains;

allowing active conjugated diene polymer chains having an active metal at a terminal thereof, which are obtained by polymerizing a conjugated diene monomer alone or both of a conjugated diene monomer and an aromatic vinyl monomer using an organic active metal, to react with a compound having in the molecule at least one functional group selected from the group consisting of a >C=O group, a >C=S group, an amino group, an imino group, an epoxy group, a pyridyl group, an alkoxyl group and a halogen, to prepare a polymer solution of the conjugated dione rubber (B) having a weight average molecular weight in the range of 1,000 to 3,000,000;

mixing together the polymer solution of the conjugated diene rubber (A) and the polymer solution of the conjugated diene rubber (B); and then, removing the liquid medium from the mixed polymer solution to recover the rubber composition.

Production Process (II):

A process for producing the above-mentioned conjugated diene rubber composition, which comprises:

allowing 5% to 95% portion of active conjugated diene polymer chains having an active metal at a terminal thereof, which are obtained by polymerizing a conjugated diene monomer alone or both of a conjugated diene monomer and an aromatic vinyl monomer using an organic active metal in an inert solvent, to react with a compound having in the molecule at least one functional group selected from the group consisting of a >C=O group, a >C=S group, an amino group, an imino group, an epoxy group, a pyridyl group, an alkoxyl group and a halogen; and then, allowing 10% to 100% of the remainder portion of the active conjugated diene polymer chains having an active metal at a terminal thereof to react with a polyorganosiloxane having a functional group capable of reacting with the active metal at a terminal of the active conjugated diene polymers; wherein the amount of the polyorganosiloxane is larger than 0.001 mole but smaller than 0.1 mole, per mole of the organic active metal in the remainder portion of the active conjugated diene polymer chains; and said polyorganosiloxane is at least one polyorganosiloxane selected from those which are represented by the formulae (1), (2) and (3), wherein $X^1$ and $X^4$ in the formula (1) are a functional group capable of reacting with an active metal at a terminal of the active conjugated diene polymer chains, or are an alkyl group having 1 to 6 carbon atoms or an aryl group having 6 to 12 carbon atoms, $X^2$ is a functional group capable of reacting with an active metal at a terminal of the active conjugated diene polymer chains, $X^3$ is a group comprising 2 to 20 alkylene glycol repeating units; and $X^5$ through $X^8$ in the formula (2) are a functional group capable of reacting with an active metal at a terminal of the active conjugated diene polymer chains; and $X^9$ through $X^{11}$ in the formula (3) are a functional group capable of reacting with an active metal at a terminal of the active conjugated diene polymer chains.

In a further aspect of the present invention, there is provided a rubber vulcanizate which is obtainable by crosslinking the above-mentioned conjugated diene rubber composition.

Effect of the Invention

The conjugated diene rubber composition according to the present invention, which comprises (A) a branched conjugated diene rubber having a structure such that at least three conjugated diene polymer chains are bonded together through a polyorganosiloxane, and (B) a conjugated diene rubber having reacted therewith a compound having a specific functional group in the molecule, exhibits improves processability, when silica is incorporated therein, and gives a rubber vulcanizate having well reduced heat build up, good wet-grip property and high abrasion resistance.

BEST MODE FOR CARRYING OUT THE INVENTION

The invention will now be described in detail.

Conjugated Diene Rubber (A)

The conjugated diene rubber (A) contained in the conjugated dione rubber composition of the present invention is a conjugated diene rubber having a weight average molecular weight in the range of 1,000 to 3,000,000 and having a structure such that at least three conjugated diene polymer chains are bonded together through at least one polyorganosiloxane (polyorganosiloxane after reaction) selected from those which are represented by the above-recited general formulae (1), (2) and (3).

Polymer chains constituting the conjugated diene rubber are preferably a homopolymer chain derived from a conjugated diene monomer or a copolymer chain derived from a conjugated diene monomer and an aromatic vinyl monomer. More specifically the polymer chains are preferably those which comprise 50% to 100% by weight of conjugated diene monomer or monomers and 50% to 0% by weight of aromatic vinyl monomer or monomers.

In view of enhanced mechanical properties, the conjugated diene polymer chains are preferably copolymer chains derived from a conjugated diene monomer and an aromatic vinyl monomer. More specifically the preferable copolymer chains comprise 50% to 95% by weight, more preferably 55% to 90% by weight and especially 60% to 85% by weight of conjugated diene monomer units and 50% to 5% by weight, more preferably 45% to 10% by weight and especially 40% to 15% by weight of aromatic vinyl monomer units.

The bonding fashion of conjugated diene monomer units and aromatic vinyl monomer units may be any of, for example, block, tapered and random copolymers.

In the case when the conjugated diene rubber is a tapered or random copolymer, the distribution of sequence in the polymer chain is not particularly limited, but the amount of a discrete single structural unit of aromatic vinyl monomer is preferably in the range of 40% to 100% by weight, more preferably 60% to 90% by weight in view of low heat build up of a resulting rubber vulcanizate. The content of a sequence composed of at least 8 structural units of aromatic vinyl monomer is preferably not larger than 10% by weight and more preferably not larger than 3% by weight.

The vinyl bond content in the conjugated diene monomer units is not particularly limited, but is usually in the range of 5% to 95% by weight, preferably 20% to 80% by weight, more preferably 30% to 70% by weight and especially preferably 35% to 65% by weight. When the vinyl bond content is relatively large, a rubber vulcanizate has well balanced reduced heat build up and wet-grip property. When the vinyl bond content is relatively medium, a rubber vulcanizate has well balanced wet-grip property and abrasion resistance.

The glass transition temperature of the conjugated diene rubber (A) is not particularly limited, but is usually in the range of −120 to 20° C., preferably −100 to −10° C. and more preferably −90 to −20° C. When the glass transition temperature is relatively high, a resulting rubber vulcanizate has excellent low heat build up, tensile strength and wet-grip property. In contrast, when the glass transition temperature is relatively low, a resulting rubber vulcanizate has excellent low heat build up, tensile strength and abrasion resistance.

The conjugated diene monomer includes, for example, 1,3-butadiene, 2-methyl-1,3-butadiene, 2,3-dimethyl-1,3-butadiene and 1,3-pentadiene. Of these, 1,3-butadiene and 2-methyl-1,3-butadiene are preferable. 1,3-Butadiene is especially preferable. These conjugated diene monomers may be used either alone or as a combination of at least two thereof.

The aromatic vinyl monomer includes, for example, styrene, α-methylstyrene, 2-methylstyrene, 3-methylstyrene, 4-methylstyrene, 2,4-diisopropylstyrene, 2,4-dimethylstyrene, 4-t-butylstyrene, 5-t-butyl-2-methylstyrene, 4-t-butoxystyrene, dimethylaminomethylstyrene and dimethylaminoethylstyrene. Of these, styrene is preferable. These aromatic vinyl monomers may be used either alone or as a combination of at least two thereof.

The above-mentioned conjugated diene polymer chain may comprise other monomer units in addition to the conjugated diene monomer units and the aromatic vinyl monomer units.

Such other monomer includes, for example, ethylenically unsaturated carboxylic acid ester monomers such as isopropyl acrylate, isopropyl methacrylate, n-butyl acrylate, n-butyl methacrylate, dimethylaminopropyl acrylate and dimethylaminopropyl methacrylate; olefin monomers such as ethylene, propylene, isobutylene and vinylcyclohexane; and non-conjugated diene monomers such as 1,4-pentadiene and 1,4-hexadiene. The amount of these monomer units is preferably not larger than 10% by weight, more preferably not larger than 5% by weight.

The conjugated diene rubber (A) has a structure such that at least three of the above-mentioned conjugated diene polymer chains are bonded together through at least one polyorganosiloxane after reaction selected from those which are represented by the general formulae (1), (2) and (3).

In the general formula (1), $R^1$ through $R^8$ represent an alkyl group having 1 to 6 carbon atoms or an aryl group having 6 to 12 carbon atoms, and $R^1$ through $R^8$ may be the same or different. $X^1$ and $X^4$ are such that (i) a part of the sum of $X^1$ and $X^4$ is a functional group capable of reacting with an active metal at a terminal of the active conjugated diene polymer chains and the remainder of the $X^1$ and $X^4$ is a group derived from said functional group or a single bond, or (ii) $X^1$ and $X^4$ are an alkyl group having 1 to 6 carbon atoms or an aryl group having 6 to 12 carbon atoms. $X^1$ and $X^4$ may be the same or different. A part of $X^2$ is a functional group capable of reacting with an active metal at a terminal of the active conjugated diene polymer chains and the remainder of $X^2$ is a group derived from said functional group or a single bond. $X^3$ is a group comprising 2 to 20 alkylene glycol repeating units, provided that a part of $X^3$ may be a group derived from the group comprising 2 to 20 alkylene glycol repeating units. m is an integer of 3 to 200, n is an integer of 0 to 200 and k is an integer of 0 to 200.

The alkyl group having 1 to 6 carbon atoms for $R^1$ through $R^8$, and $X^1$ and $X^4$ includes, for example, a methyl group an ethyl group, an n-propyl group, an isopropyl group, a butyl group, a pentyl group, a hexyl group and a cyclohexyl group. The aryl group having 6 to 12 carbon atoms includes, for example, a phenyl group and a methylphenyl group. Of these alkyl and aryl groups, a methyl group is preferable.

The functional group capable of reacting with an active metal at a terminal of the active conjugated diene polymer chains for $X^1$, $X^2$ and $X^4$ preferably includes an alkoxyl group having 1 to 5 carbon atoms, and a hydrocarbon group having a 2-pyrrolidonyl group and a group having 4 to 12 carbon atoms and containing an epoxy group.

By the term "a group derived from said functional group (i.e., the functional group capable of reacting with an active metal at a terminal of the active conjugated diene polymer chains)" for $X^1$, $X^2$ and $X^4$, we mean a residual group which 16 formed from said functional group by the reaction of said functional group with the active metal when the active conjugated diene polymer chains having the active metal at a terminal thereof are allowed to react with the polyorganosiloxane having said functional group.

The alkoxyl group having 1 to 5 carbon atoms includes, for example, a methoxy group, an ethoxy group, a propoxy group, an isopropoxy group and a butoxy group. Of these, methoxy group is preferable.

The hydrocarbon group having a 2-pyrrolidonyl group preferably includes, those which are represented by the following general formula (4).

General formula (4):

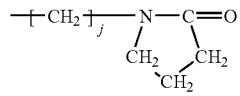

wherein j is an integer of 2 to 10.

The group having 4 to 12 carbon atoms and containing an epoxy group includes those which are represented by the following formula (5):

ZYE wherein Z is an alkylene group or an alkylarylene group, which have 1 to 10 carbon atoms, Y is a methylene group, a sulfur atom or an oxygen atom, and E is a group having 4 to 12 carbon atoms and containing an epoxy group. Of the groups of formula (5), those in which Y is an oxygen atom are preferable. Those in which Y is an oxygen atom and E is a glycidyl group are more preferable. Those in which Z is an alkylene group having 3 carbon atoms, Y is an oxygen atom and E is a glycidyl group are especially preferable.

In the general formula (1), when a part of $X^1$ and/or $X^4$ is a group selected from an alkoxyl group having 1 to 5 carbon atoms, a hydrocarbon group having a 2-pyrrolidonyl group, and a group having 4 to 12 carbon atoms and containing an epoxy group, the remainder of $X^1$ and/or $X^4$ is a group derived from said functional group or a single bond. $X^2$ is such that a part of $X^2$ is a functional group capable of reacting with an active metal at a terminal of the active conjugated diene polymer chains and the remainder of $X^2$ is a group derived from said functional group or a single bond.

In the polyorganosiloxane before reaction represented by the general formula (1), in the case where at least a part of $X^1$, $X^2$ and $X^4$ is an alkoxyl group having 1 to 5 carbon atoms, when the active conjugated diene polymer chains are allowed to react with the polyorganosiloxane, the bond between a silicon atom and an oxygen atom in the alkoxyl group is cleaved whereby the active conjugated dione polymer chain is directly bonded to the silicon atom to form a single bond. That is, in the polyorganosiloxane after reaction represented by the formula (1), a part of $X^1$, $X^2$ and $X^4$ is a single bond.

In the polyorganosiloxane before reaction represented by the general formula (1), in the case where at least a part of $X^1$, $X^2$ and $X^4$ is a hydrocarbon group having a 2-pyrrolidonyl group, when the active conjugated diene polymer chains are allowed to react with the polyorganosiloxane, the carbon-oxygen bond in the carbonyl group of 2-pyrrolidonyl group is cleaved to form a structure such that the active conjugated diene polymer chain is directly bonded to the carbon atom.

In the polyorganosiloxane before reaction represented by the general formula (1), in the case where at least a part of $X^1$, $X^2$ and $X^4$ is a group having 4 to 12 carbon atoms and containing an epoxy group, when the active conjugated diene polymer chains are allowed to react with the polyorganosiloxane, the oxygen-carbon bond in the epoxy group is cleaved to form a structure such that the active conjugated diene polymer chain is bonded to the carbon atom.

In the polyorganosiloxane after reaction represented by the general formula (1), among the groups for $X^1$ and $X^4$, a group having 4 to 12 carbon atoms and containing an epoxy group, and a group derived from said group having 4 to 12 carbon atoms and containing an epoxy group, and an alkyl group having 1 to 6 carbon atoms are preferable. Among the groups for $X^2$, a group having 4 to 12 carbon atoms and containing an epoxy group, and a group derived from said group having 4 to 12 carbon atoms and containing an epoxy group are preferable.

In the polyorganosiloxane after reaction represented by the general formula (1), the group comprising 2 to 20 alkylene glycol repeating units for $X^3$ is preferably a group represented by the following general formula (6), General formula (6):

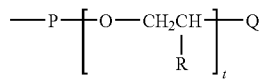

wherein t is an integer of 2 to 20, P is an alkylene group or an alkylarylene group, which have 2 to 10 carbon atoms, R is a hydrogen atom or a methyl group, Q is an alkoxyl group or an aryloxy group, which have 1 to 10 carbon atoms, provided that a part of Q may be a single bond. Of these, those in which t is an integer of 2 to 8, P is an alkylene group having 3 carbon atoms, R is a hydrogen atom and Q is a methoxy group are preferable.

In the polyorganosiloxane represented by the formula (1), m is an integer of 3 to 200, preferably 20 to 150 and more preferably 30 to 120. When m is too small, a vulcanizable conjugated diene rubber composition having incorporated therein silica tends to have poor processability and a rubber vulcanizate thereof is sometimes poor in the balance between abrasion resistance and low heat build up. When m is too large, the polyorganosiloxane is difficult to prepare, and is too viscous to handle.

n is an integer of 0 to 200, preferably 0 to 150 and more preferably 0 to 120. k is an integer of 0 to 200, preferably 0 to 150 and more preferably 0 to 120.

The total of m, n and k is preferably not more than 400, more preferably not more than 300 and especially preferably not more than 250. When the total of m, n and k is too large, the polyorganosiloxane is difficult to prepare, and is too viscous to handle.

In the polyorganolioxane after reaction represented by the formula (2), $R^9$ through $R^{16}$ represent an alkyl group having 1 to 6 carbon atoms or an aryl group having 6 to 12 carbon atoms, and $R^9$ through $R^{16}$ may be the same or different. $X^5$ through $X^8$ are such that a part of the sum of $X^5$ through $X^8$ is a functional group capable of reacting with an active metal at a terminal of the active conjugated diene polymer chains and the remainder of the sum of $X^5$ through $X^8$ is a group derived from said functional group or a single bond.

In the polyorganolioxane after reaction represented by the formula (3), $R^{17}$, $R^{18}$ and $R^{19}$ represent an alkyl group having 1 to 6 carbon atoms or an aryl group having 6 to 12 carbon atoms, and $R^{17}$, $R^{18}$ and $R^{19}$ may be the same or different. $X^9$, $X^{10}$ and $X^{11}$ are such that a part of the sum of $X^9$, $X^{10}$ and $X^{11}$ is a functional group capable of reacting with an active metal at a terminal of the active conjugated diene polymer chains and the remainder of the sum of $X^9$, $X^{10}$ and $X^{11}$ is a group derived from said functional group or a single bond. s is an integer of 1 to 18.

In the polyorganosiloxanes after reaction represented by the formulae (2) and (3), as specific examples of the alkyl group having 1 to 6 carbon atoms, the aryl group having 6 to 12 carbon atoms, and the functional group capable of reacting with an active metal at a terminal of the active conjugated diene polymer chains, and the group derived from said functional group, there can be mentioned those which are recited for the polyorganosiloxanes after reaction represented by the formula (1).

The branched conjugated diene polymers constituting the conjugated diene rubber (A) preferably has a structure such that at least four of the conjugated diene polymer chains are bonded together through the polyorganosiloxane. More specifically, the conjugated diene rubber (A) preferably comprises 2% to 90% by weight, more preferably 5% to 80% by weight, based on the conjugated diene rubber (A), of a conjugated diene rubber having a structure such that at least four of the conjugated diene polymer chains are bonded together through the polyorganosiloxane.

In the case where the conjugated diene rubber (A) comprises the branched conjugated diene polymers having a structure such that at least four of the conjugated diene polymer chains are bonded together through the polyorganosiloxane, the conjugated diene rubber (A) exhibits good coagulability and good drying property in the step of producing the rubber composition according to the present invention; and, when silica is incorporated therein, the vulcanizable rubber composition exhibits more improved processability and gives a rubber vulcanizate better balanced in low heat build up, wet grip property and abrasion resistance.

The weight average molecular weight of the conjugated diene rubber (A) is appropriately chosen in the range of 1,000 to 3,000,000, preferably 10,000 to 2,000,000 and more preferably 300,000 to 1,200,000. When the molecular weight is too high, the incorporation of silica tends to become difficult and the silica-incorporated vulcanizable rubber composition is liable to have poor processability. In contrast, when the molecular weight is too low, a resultant rubber vulcanizate tends to have heat build up which is not reduced to the desired extent, and the production cost is liable to be increased.

Especially when the conjugated diene rubber (A) is incorporated as solid rubber in the rubber composition of the present invention, the weight average molecular weight of the conjugated diene rubber (A) is chosen usually in the range of 100,000 to 3,000,000, preferably 150,000 to 2,000,000 and more preferably 200,000 to 1,500,000. It also is possible that the conjugated diene rubber (A) is incorporated as liquid rubber in combination with other solid rubber to appropriately adjust the viscosity of kneading mixture, enhance the dispersibility of a filler, and give a rubber vulcanizate having improved wet-grip property. In this case, the weight average molecular weight of the conjugated diene rubber (A) is chosen usually in the range of 3,000 to 100,000, preferably 10,000 to 80,000 and more preferably 30,000 to 70,000.

The amount of the conjugated diene rubber (A) contained in the conjugated diene rubber composition of the present invention is in the range of 5% to 95% by weight, preferably 7% to 80% by weight and more preferably 10% to 75% by weight, based on the total weight of conjugated diene rubber composition. When the amount of the conjugated diene rubber (A) is too small, a silica-incorporated vulcanizable rubber composition has poor processability, and a resulting rubber vulcanizate exhibits a heat build up, which is not reduced to the desired extent, and is poor in other physical properties. In contrast, a rubber composition containing a large amount of the conjugated diene rubber (A) is usually difficult to prepare.

Conjugated Diene Rubber (B)

The conjugated diene rubber (B) contained in the conjugated diene rubber composition of the present invention is a conjugated diene rubber having a weight average molecular weight in the range of 1,000 to 3,000,000 and having a structure such that it has been allowed to react with a compound having in the molecule at least one functional group selected from the group consisting of a >C=O group, a >C=S group, an amino group, an imino group, an epoxy group, a pyridyl group, an alkoxyl group and a halogen. The conjugated diene rubber (B) comprises at least one of the two types of conjugated diene rubbers, one of which has a structure such that two conjugated diene polymer chains are bonded together through the above-mentioned functional group, and the other of which has a structure such that the above-mentioned functional group is bonded to a terminal of conjugated diene polymer chain.

As specific examples of the compound having a >C=O group, there can be mentioned N-substituted cyclic amides such as N-methyl-2-pyrrolidone, N-vinyl-2-pyrrolidone, N-phenyl-2-pyrrolidone and N-methyl-ε-caprolactam; N-substituted cyclic ureas such as 1,3-dimethylethyleneurea and 1,3-diethyl-2-imidazolidinone; N-substituted amino ketones such as 4,4'-bis(dimethylamino)benzophenone and 4,4'-bis(diethylamino)benzophenone; and aromatic isocyanates such as diphenylmethane diisocyanate and 2,4-tolylene diisocyanate.

Of these, N-substituted cyclic amides, N-substituted cyclic ureas and N-substituted amino ketones are preferable. More specifically N-vinyl-2-pyrrolidone. N-phenyl-2-pyrrolidone, N-methyl-ε-caprolactam, 1,3-diethyl-2-imidazolidinone and 4,4'-bis(diethylamino)benzophenone are especially preferable.

As specific examples of the compound having a >C=S group, there can be mentioned N,N,N',N'-tetramethylthiourea.

As specific examples of the compound having an amino group, there can be mentioned N,N-disubstituted aminoalkylmethacrylamides such as N,N-dimethylaminopropylmethacrylamide; and N-substituted aminoaldehydes such as 4-N,N-dimethylaminobenzaldehyde.

As specific examples of the compound having an imino group, there can be mentioned N-substituted carbodiimides such as dicyclohexylcarbodiimide; and Schiff bases such as N-ethylethylideneimine and N-methylbenzylideneimine.

As specific examples of the compound having an epoxy group, there can be mentioned propylene oxide, tetraglycidyl-1,3-bisaminomethylcyclohexane and epoxidized polybutadiene.

As specific examples of the compound having a pyridyl group, there can be mentioned vinyl compounds having a pyridyl group such as 4-vinylpyridine.

As specific examples of the compound having an alkoxyl group, there can be mentioned bis(triethoxysilylpropyl)-tetrasulfide, bis(tributoxysilylpropyl)tetrasulfide, γ-glydoxypropyltrimethoxysilane, and tetramethoxysilane.

As specific examples of the compound having a halogen, there can be mentioned tin tetrachloride, silicon tetrachloride, triphenylmonochlorotin, triphenoxychlorosilane, methyltriphenoxysilane and diphenoxydichlorosilane.

The conjugated diene polymer chains constituting the conjugated diene rubber (B) are preferably a homopolymer chain derived from a conjugated diene monomer or a copolymer chain derived from a conjugated diene monomer and an aromatic vinyl monomer, which is similar to the conjugated diene polymer chain constituting the conjugated diene polymer (A). More specifically the polymer chains are preferably those which comprise 50% to 100% by weight of conjugated diene monomer or monomers and 0% to 50% by weight of aromatic vinyl monomer or monomers. If desired, the conjugated diene polymer chains may comprise units derived from monomers other than a conjugated diene monomer and an aromatic vinyl monomer. The kinds and amounts of such other monomers can be chosen as mentioned for the conjugated diene polymer chains for the conjugated diene rubber (A).

The weight average molecular weight of the conjugated diene rubber (B) is appropriately chosen in the range of 1,000 to 3,000,000, preferably 10,000 to 2,000,000 and more preferably 300,000 to 1,200,000, which is similar to the conjugated diene rubber (A). When the molecular weight is too high, the incorporation of silica tends to become difficult and the silica-incorporated vulcanizable rubber composition is liable to have poor processability. In contrast, when the molecular weight is too low, a resultant rubber vulcanizate tends to have heat build up which is not reduced to the desired extent, and the production cost is liable to be increased.

When the conjugated diene rubber (B) is incorporated as solid rubber in the rubber composition of the present invention, the weight average molecular weight of the conjugated diene rubber (B) is chosen usually in the range of 100,000 to 3,000,000, preferably 150,000 to 2,000,000 and more preferably 200,000 to 1,500,000. It also is possible that the conjugated diene rubber (B) is incorporated as liquid rubber in combination with other solid rubber to appropriately adjust the viscosity of kneading mixture, enhance the dispersibility of a filler, and give a rubber vulcanizate having improved wet-grip property. In this case, the weight average molecular weight of the conjugated diene rubber (B) is chosen usually in the range of 3,000 to 100,000, preferably 10,000 to 80,000 and more preferably 30,000 to 70,000.

The amount of the conjugated diene rubber (B) contained in the conjugated diene rubber composition of the present invention is in the range of 5% to 95% by weight, preferably 70 to 80% by weight and more preferably 10% to 60% by weight, based on the total weight of conjugated diene rubber composition. When the amount of the conjugated diene rubber (B) is too small, a silica-incorporated vulcanizable rubber composition has poor processability, and a resulting rubber vulcanizate exhibits a heat build up, which is not reduced to the desired extent, and is poor in other physical properties. In contrast, a rubber composition containing a large amount of the conjugated diene rubber (B) gives a rubber vulcanizate exhibits a heat build up, which is not reduced to the desired extent, and has poor abrasion resistance.

Process for Producing Conjugated Diene Rubber (A) and Conjugated Diene Rubber (B), and Process for Producing Conjugated Diene Rubber Composition The conjugated diene rubber (A) is produced by allowing active conjugated diene polymer chains having an active metal at a terminal thereof, which are obtained by polymerizing a conjugated diene monomer alone or both of a conjugated diene monomer and an aromatic vinyl monomer using an organic active metal in an inert solvent, to react with a polyorganosiloxane having a functional group capable of reacting with the active metal at a terminal of the active conjugated diene polymers in an inert solvent. The polyorganosiloxane is at least one polyorganosiloxane selected from those which are represented by the above-mentioned formulae (1), (2) and (3) (polyorganosiloxanes before reaction).

The conjugated diene rubber (B) is produced by allowing active conjugated diene polymer chains having an active metal at a terminal thereof, which are obtained by polymerizing a conjugated diene monomer alone or both of a conjugated diene monomer and an aromatic vinyl monomer using an organic active metal in an inert solvent, to react with a compound having in the molecule at least one functional group selected from the group consisting of a >C=O group, a >C=S group, an amino group, an imino group, an epoxy group, a pyridyl group, an alkoxyl group and a halogen in an inert solvent.

The conjugated diene rubber composition according to the present invention can be produced by mixing together the separately produced conjugated diene rubber (A) and conjugated diene rubber (B) (which production process is hereinafter referred to as "first production process for the conjugated diene rubber composition" when appropriate).

As an alternative process, the conjugated diene rubber composition according to the present invention can be produced by allowing a portion of active conjugated diene polymer chains having an active metal at a terminal thereof, which are obtained as mentioned above, to react with one of (i) at least one polyorganosiloxane having a functional group capable of reacting with the active metal at a terminal of the active conjugated diene polymers, which is selected from those (polyorganosiloxanes before reaction) which are represented by the above-mentioned formulae (1), (2) and (3), and (ii) a compound having in the molecule at least one functional group selected from the group consisting of a >C=O group, a >C=S group, an amino group, an imino group, an epoxy group, a pyridyl group, an alkoxyl group and a halogen in an inert solvent; and then, allowing the remainder portion of the active conjugated diene polymer chains having an active metal at a terminal thereof to react with the other of (i) and (ii) (which production process is hereinafter referred to as "second production process for the conjugated diene rubber composition" when appropriate).

In the second production process for the conjugated diene rubber composition, in the case when the polyorganosiloxane used is that is represented by the formula (1) wherein m/k is at least 0.2, or that is represented by the formula (2) or (3), it is preferable that a portion of the active conjugated diene polymer chains having an active metal at a terminal thereof is first allowed to react with (ii) a compound having in the molecule at least one functional group selected from the group consisting of a >C=O group, a >C=S group, an amino group, an imino group, an epoxy group, a pyridyl group, an alkoxyl group and a halogen in an inert solvent; and then, the remainder portion of the active conjugated diene polymer chains having an active metal at a terminal thereof is allowed to react with (i) at least one polyorganosiloxane having a functional group capable of reacting with the active metal at a terminal of the active conjugated diene polymers, which is selected from those (polyorganosiloxanes before reaction) of the above-mentioned formulae (1), (2) and (3). If the reaction order is reverse, a resulting rubber vulcanizate tends to exhibit a heat build up, which is low, but reduced only to insufficient extent, and have an abrasion resistance improved only to a minor extent.

The amount of the conjugated diene monomer used, or the total amount of the conjugated diene monomer plus aromatic vinyl monomer can be appropriately chosen so that the finally obtained conjugated diene rubber contains the desired amounts of the monomer units.

The inert solvent used at the polymerization using an organic active metal is not particularly limited, provided that it is usually used and does not give a harmful influence on the polymerization reaction. As specific examples of the inert solvent, there can be mentioned aliphatic hydrocarbons such as butane, pentane, hexane and 2-butene; alicyclic hydrocarbons such as cyclopentane, cyclohexane and cyclohexene; and aromatic hydrocarbons such as benzene, toluene and xylene. The amount of inert solvent is determined so that the concentration of monomer is usually in the range of 1% to 50% by weight, preferably 10% to 40% by weight.

The organic active metal used includes, for example, organic alkali metal compounds, organic alkaline earth metal compounds and organic transition metal compounds. Of these, organic alkali metal compounds are preferably used, and, as specific examples thereof, there can mentioned organic monolithium compounds such as n-butyllithium, sec-butyllithium, t-butyllithium, hexyllithium, phenyllithium and stilbenelithium; organic poly-lithium compounds such as dilithiomethane, 1,4-dilithiobutane, 1,4-dilithio-2-ethylcyclohexane and 1,3,5-trilithiobenzene; organic sodium compounds such as sodium naphthalene; and organic potassium compounds such as potassium naphthalene. Of these, organic lithium compounds are preferable. Organic monolithium compound is especially preferable. Organic alkali metal compounds may be previously reacted with a secondary amine such as dibutylamine, dihexylamine, dibenzylamine or pyrrolidine, to form an organic alkali metal amide compound, prior to the use in polymerization. These organic alkali metal compounds may be used either alone or as a combination of at least two thereof.

The amount of organic active metal is preferably in the range of 1 to 50 milli-mole, more preferably 2 to 20 milli-mole, per 1,000 g of the monomer mixture.

To produce a conjugated diene polymer containing conjugated diene monomer units having the desired vinyl bond content, a polar compound is preferably added in a polymerization mixture. The polar compound includes, for example, ether compounds such as dibutyl ether and tetrahydrofuran; tertiary amines such as tetraethylethylenediamine; alkali metal alkoxides; and phosphine compounds. Of these, ether compounds and tertiary amines are preferable. Tertiary amines are more preferable. Tetraethylethylenediamine is especially preferable. The amount of polar compound used is preferably in the range of 0.01 to 100 moles, more preferably 0.3 to 30 moles, per mole of the organic active metal. By using the polar compound, the content of vinyl bond in the conjugated diene monomer units can be easily adjusted and an undesirable deactivation of a catalyst can be avoided.

The polymerization temperature is usually in the range of −78 to 150° C., preferably 0 to 100° C. and more preferably 30 to 90° C.

The polymerization manner may be any of a batchwise manner, a continuous manner and others. To obtain a conjugated diene polymer containing conjugated diene monomer units having a relatively high vinyl bond content, a batchwise manner is advantageously adopted. To obtain a polymer with a relatively low or medium vinyl bond content, a continuous manner is advantageously adopted.

In the case when a conjugated diene monomer is copolymerized with an aromatic vinyl monomer, in order to enhance the randomness of the bond between the conjugated diene monomer units and the aromatic vinyl monomer units, a conjugated diene monomer or a mixture of a conjugated diene monomer and an aromatic vinyl monomer unit is preferably incorporated continuously or intermittently in a polymerization mixture so that the relative proportion of aromatic vinyl monomer in the sum of conjugated diene monomer and aromatic vinyl monomer is kept in a specific range.

For the production of the conjugated diene rubber (A), the active conjugated diene polymer chains having an active metal at a terminal thereof, which are obtained by the above-mentioned polymerization process, is allowed to react with a polyorganosiloxane having a functional group capable of reacting with the active metal at a polymer terminal.

The polyorganosiloxane is at least one polyorganosiloxane selected from those which are represented by the above-mentioned formulae (1), (2) and (3), wherein $X^1$ and $X^4$ in the formula (1) are a functional group capable of reacting with an active metal at a terminal of the active conjugated diene polymer chains, or are an alkyl group having 1 to 6 carbon atoms or an aryl group having 6 to 12 carbon atoms, $X^2$ is a functional group capable of reacting with an active metal at a terminal of the active conjugated diene polymer chains, $X^3$ is a group comprising 2 to 20 alkylene glycol repeating units; and $X^5$ through $X^8$ in the formula (2) are a functional group capable of reacting with an active metal at a terminal of the active conjugated diene polymer chains; and $X^9$ through $X^{11}$ in the formula (3) are a functional group capable of reacting with an active metal at a terminal of the active conjugated diene polymer chains.

The above-mentioned polyorganosiloxane can be prepared by, for example, the methods described in "Lecture on Experimental Chemistry" vol. 28, fourth edition, edited by the Chemical Society of Japan, and the methods described in the references cited therein. The polyorganosiloxane also is commercially available.

The amount of polyorganosiloxane is larger than 0.001 mole, but smaller than 0.1 mole, preferably larger than 0.005 mole, but smaller than 0.09 mole, and more preferably larger than 0.01 mole but smaller than 0.08 mole, per mole of the organic active metal used for polymerization. When the amount of polyorganosiloxane is too large or too small, a branched conjugated diene polymer is difficult to form, and the desired effect according to the present invention is difficult to obtain.

The polyorganosiloxane is preferably incorporated in the polymerization mixture whereby the polyorganosiloxane is dissolved in the inert solvent used for polymerization, and thus, a uniform reaction is liable to occur between the active metal at a terminal of active conjugated diene polymer chains and the polyorganosiloxane. The amount of polyorganosiloxane is such that the content thereof in the solution is in the range of 1% to 50% by weight.

The time at which the active conjugated diene polymer chains are allowed to react with the polyorganosiloxane is preferably when the polymerization reaction is substantially completed, and more specifically, after the polymerization reaction is substantially completed, but before the formed active conjugated diene polymer chains are subjected to side reactions to be thereby gelled, or subjected to a chain transfer reaction due to the impurities present in the polymerization mixture.

Prior to the commencement of reaction between the active conjugated diene polymer chains and the polyorganosiloxane, a polymerization stopper, a polymer terminal-modifier, or a coupling agent can be incorporated in the polymerization mixture whereby a portion of the active metal at a terminal of the active conjugated diene polymer is deactivated, provided that the desired effect of the present invention is not injured. The polymerization stopper, the polymer terminal-modifier and the coupling agent may be conventionally used in anion polymerization.

The reaction between the active conjugated diene polymer chains and the polyorganosiloxane is carried out usually at a temperature in the range of 0 to 100° C. preferably 30 to 90° C., usually for 1 to 120 minutes, preferably 2 to 60 minutes.

When the polymerization between the active conjugated diene polymer chains and the polyorganosiloxane proceeds to the desired extent, a polymerization stopper is added to stop the reaction whereby a solution of the desired branched polymer is obtained. The polymerization stopper includes, for example, alcohols such as methanol and isopropanol, and water.

In the case when unreacted active conjugated diene polymer chains remain after the reaction between the active conjugated diene polymer chains and the polyorganosiloxane is conducted, if desired, prior to the addition of a polymerization stopper, a polymer terminal modifier or a coupling agent may be added into the polymerization mixture to modify the polymer. The polymer terminal modifier and the coupling agent may be conventionally used in anion polymerization.

The conjugated diene rubber (B) is produced by substantially the same process as that adopted for the production of the conjugated diene rubber (A) except that a compound having in the molecule at least one functional group selected from the group consisting of a >C=O group, a >C=S group, an amino group, an imino group, an epoxy group, a pyridyl group, an alkoxyl group and a halogen is used instead of the polyorganosiloxane. The compound having such functional group may be used either alone or as a combination of at least two thereof.

In the second production process for the conjugated diene rubber composition according to the present invention wherein active conjugated diene polymer chains having an active metal at a terminal thereof, which are obtained as mentioned above, are allowed to react with one of (i) the above-mentioned polyorganosiloxane of the formula (1), (2) or (3), and (ii) a compound having the above-mentioned functional group capable of reacting with the active metal at a terminal of the active conjugated diene polymer chains, and then, allowed to react with the other of (i) and (ii), in the case when the polyorganosiloxane used contains a relatively large amount of functional groups capable of reacting with the active metal at a terminal of the conjugated diene polymer chains [that is, in the case when the polyorganosiloxane is represented by the formula (1) wherein m/k is at least 0.2, or represented by the formula (2) or (3)], it is preferable that a portion of the active conjugated diene polymer chains having an active metal at a terminal thereof is first allowed to react with the compound having in the molecule the functional group capable of reacting with the active metal at a terminal of the conjugated diene polymer chains to form the conjugated diene rubber (B), and then, the remainder portion of the active conjugated diene polymer chains having an active metal at a terminal thereof is allowed to react with the above-mentioned polyorganosiloxane to form the conjugated diene rubber (A). If the reaction order is reverse, that is, the active conjugated diene polymer chains are first allowed to react with the above-mentioned polyorganosiloxane to form the conjugated diene rubber (A), and then allowed to react with the compound having in the molecule the functional group capable of reacting with the active metal at a terminal of the conjugated diene polymer chains, it is difficult to produce the desired amount of conjugated diene rubber (B), and a resulting rubber vulcanizate tends to exhibit a heat build up, which is reduced only to insufficient extent, and have an abrasion resistance improved only to a minor extent.

In the production of the conjugated diene rubber (B), the modification ratio, i.e., the ratio of the polymer chains having introduced therein the above-mentioned functional group to the polymer chains having the active metal at a terminal thereof used for the reaction with the functional group is preferably in the range of 5% to 95% by mole, based on the active metal-having terminal. In general, the larger this modification ratio is, the more satisfactory the wet-grip property and low heat build up of a resultant rubber vulcanizate are. The modification ratio is determined by calculating the ratio (UV/RI) of the ultraviolet absorption intensity (UV) as measured by ultraviolet-visible light spectrophotometer to the differential refractive index (RI) as measured by the differential refractometer according to GPC, and determining the modification ratio by a previously made calibration curve.

In the second production process for the conjugated diene rubber (B), a part or the entirety of the conjugated diene rubber (B) is occasionally coupled. The coupling ratio can be determined from the peaks as measured by the differential refractometer according to GPC before and after the coupling reaction. That is, the coupling ratio is expressed by the ratio of the area (A) of peak as observed after the coupling reaction occurring on the higher molecular weight side to the position of peak as observed before the coupling reaction, to the area (B) of peak occurring at the same position as that of peak as observed before the coupling reaction.

After the production of the conjugated diene rubber (A) and/or the conjugated diene rubber (B), if desired, an antioxidant such as a phenolic antioxidant, a phosphorus-containing oxidant or a sulfur-containing antioxidant, a crumb-forming agent or a scale-preventing agent can be added to the polymerization solution, and then, a polymerization medium is removed from the polymerization solution by direct drying or steam-stripping, to give the aimed rubber (A) and/or (B). It is also be possible to add an extender oil to the polymerization solution prior to the removal of polymerization medium from the polymerization solution, whereby an oil-extended rubber is finally recovered.

As the extender oil, a process oil, mentioned below, can be used. The amount of extender oil is usually in the range of 5 to 100 parts by weight, preferably 10 to 60 parts by weight and more preferably 20 to 50 parts by weight, based on 100 parts by weight of the total rubber, i.e., the conjugated diene rubber (A) and/or the conjugated diene rubber (B).

Conjugated Diene Rubber Composition

The conjugated diene rubber composition of the present invention comprises 5% to 95% by weight of the conjugated diene rubber (A) and 95% to 5% by weight of the conjugated diene rubber (B).

The ratio (A)/(B) in amount by weight of the conjugated diene rubber (A) to the conjugated diene rubber (B) is usually chosen within the range of 5/95 to 95/5, preferably 7/93 to 93/7 and more preferably 10/90 to 85/15. If the (A)/(B) weight ratio is outside this range, the desired rubber vulcanizate having desirably low heat build up, good wet-grip property, good abrasion resistance and high tensile strength is difficult to obtain. Especially when silica and carbon black are added in combination, the reduction of heat build up becomes poor.

In the production of the conjugated diene rubber (A) and the conjugated diene rubber (B), the following polymeric ingredients are generally contained, in addition to the conjugated diene rubber (A) and the conjugated diene rubber (B), in the polymerization mixture, which ingredients include a coupled polymer comprised of two conjugated diene polymer chains bonded together through the polyorganosiloxane, a polyorganosiloxane-modified conjugated diene polymer having a structure such that one polyorganosiloxane is bonded to a terminal of the conjugated diene polymer chain, a conjugated diene polymer having no organosiloxane bonded thereto, a modified conjugated diene polymer which is formed by the modification of the conjugated diene polymer with a polymer terminal modifier conventionally used in anion polymerization, and a coupled polymer which is formed by coupling of the conjugated diene polymer chains with a coupling agent conventionally used in anion polymerization. The conjugated diene rubber composition of the present invention may comprise these polymeric ingredients.

Further, the conjugated diene rubber composition of the present invention can have incorporated therein a polymer having a glass transition temperature in the range of −120° C. to 200° C., and a weight average molecular weight in the range of 1,000 to 3,000,000.

The polymer to be incorporated is chosen from resinous polymers and rubbery polymers, which have a weight average molecular weight in the above-recited range, preferably 300,000 to 2,000,000, more preferably 100,000 to 1,200,000. A rubbery polymer is preferable. The rubbery polymer may be a conjugated diene rubbery polymer having a glass transition temperature usually in the range of −110° C. to 100° C., preferably −110° C. to −10° C. and more preferably −110° C. to −25° C. If the glass transition temperature is too high, a resulting rubber vulcanizate tends to exhibit a heat build up, which is low but is not reduced to the desired extent, and have an insufficient abrasion resistance.

As specific examples of the rubbery polymer to be incorporated, there can be mentioned natural rubber, a polyisoprene rubber, an emulsion-polymerized styrene-butadiene copolymer rubber, a solution-polymerized styrene-butadiene copolymer rubber (for example, such copolymer rubber having a bound styrene content in the range of 5% to 50 by weight and the 1,3-butadiene units having a 1,2-bond content in the range of 10% to 80% by weight), a polybutadiene rubber or a styrene-butadiene copolymer rubber, wherein the 1,3-butadiene units have a high trans-bond content, i.e., a trans-bond content in the range of 70% to 95% by weight, a polybutadiene rubber having a low cis-bond content, a polybutadiene rubber having a high cis-bond content, a styrene-isoprene copolymer rubber, a butadiene-isoprene copolymer rubber, a styrene-isoprene-butadiene copolymer rubber, a styrene-acrylonitrile-butadiene copolymer rubber, an acrylonitrile-butadiene copolymer rubber, a polystyrene-polybutadiene-polystyrene block copolymer rubber, an acrylic rubber, an epichlorhydrin rubber, a fluororubber, a silicone rubber, an ethylene-propylene rubber and an urethane rubber. Of these, natural rubber, a polyisoprene rubber, a polybutadiene rubber and a styrene-butadiene copolymer rubber. These rubbery polymers may be used either alone or as a combination of at least two thereof.

The amount of the above-recited polymers is usually not larger than 900 parts by weight, preferably not larger than 700 parts by weight and more preferably not larger than 500 parts by weight, based on 100 parts by weight of the total of the conjugated diene rubber (A) and the conjugated diene rubber (B). When the amount of the polymers is too large, a vulcanizable rubber composition tends to have poor processability, and a resultant rubber vulcanizate tends to exhibit heat build up which is not reduced to the desired extent, and have poor wet-grip property and abrasion resistance.

The conjugated diene rubber composition of the present invention preferably comprise at least one filler selected from silica and carbon black. Especially preferably the composition comprise silica or both of silica and carbon black as filler.

The silica includes, for example, dry-process white carbon, wet-process white carbon and colloidal silica. Of these, wet-process white carbon predominantly comprised of hydrated silicate is preferable. A carbon-silica dual phase filler having a structure such that silica is supported on the surface of carbon black can also be used. These silica fillers may be used either alone or as a combination of at least two thereof. Silica preferably has a nitrogen adsorption specific surface area in the range of 50 to 400 $m^2/g$, more preferably 100 to 220 $m^2/g$, as measured by a BET method according to ASTM D3037-81. When silica has a specific surface area falling within this range, a resulting rubber vulcanizate has more enhanced abrasion resistance and exhibits more reduced heat build up.

When silica is incorporated, further reduced heat build up and further enhanced abrasion resistance can be imparted to a rubber vulcanizate by incorporating a silane coupling agent.

As specific examples of the silane coupling agent, there can be mentioned vinyltriethoxysilane, β-(3,4-epoxycyclohexyl) ethyltrimethoxysilane, N-(β-aminoethyl)-γ-aminopropyltrimethoxysilane, 3-octathio-1-propyltriethoxysilane, bis[3-(triethoxysilyl)propyl]disulfide, bis[3-(triethoxysilyl) propyl]tetrasulfide, γ-trimethoxysilylpropyldimethylthiocarbamyltetrasulfide and γ-trimethoxysilylpropylbenzothiazyltetrasulfide. Of these, sulfides having not more than 4 carbon atoms in the molecule are preferable because scorch can be avoided at kneading. These silane coupling agents can be used either alone or as a combination of at least two thereof.

The amount of silane coupling agent incorporated is preferably in the range of 0.1 to 30 parts by weight, more preferably 1 to 15 parts by weight, based on 100 parts by weight of silica.

The carbon black includes, for example, furnace black, acetylene black, thermal black, channel black, graphite, graphite fiber and fullerene. Of these, furnace black is preferable, and, as specific examples thereof, there can be mentioned SAF, ISAP, ISAF-HS, ISAF-LS, IISAF-HS, HAF, HAF-HS, HAP-LS and FEF. The carbon black may be incorporated either alone or as a combination of at least two thereof.

The carbon black preferably has a nitrogen adsorption specific surface area ($N_2SA$) in the range of 5 to 200 $m^2/g$, more preferably 80 to 130 $m^2/g$, as measured by a BET method according to ASTM D3037-81, and preferably has a dibutyl phthalate (DBP) adsorption in the range of 5 to 300 ml/100 g, more preferably 80 to 160 ml/100 g. When carbon black has an $N_2SA$ and a DBP adsorption which fall within these ranges, a resulting rubber vulcanizate has enhanced mechanical properties and abrasion resistance.

As the carbon black, high structure carbon black as described in Japanese Unexamined Patent Publication No. H5-230290 can be used which has a cetyltrimethylammonium bromide (CTAB) adsorption specific surface area in the range of 110 to 170 $m^2/g$, and a DBP (24M4 DBP) oil adsorption in the range of 110 to 130 ml/100 g as measured after compression under 165 MPa was repeated 4 times. By using this high structure carbon black, the abrasion resistance of a rubber vulcanizate is further enhanced.

The amount of filler incorporated is preferably in the range of 5 to 150 parts by weight, more preferably 20 to 120 parts by weight and especially preferably 40 to 100 parts by weight, based on the weight of the total rubbers. If the amount of filler is too small, the effect of improving reinforcement is insufficient and a rubber vulcanizate has abrasion resistance which has not improved to the desired extent. In contrast, if the amount of filler is too large, a vulcanizable rubber composition exhibits insufficient processability and a rubber vulcanizate exhibits heat build up which is not reduced to the desired extent.

The filler can be incorporated to a solid rubber by a dry kneading method, or to a polymer solution by a wet kneading method followed by coagulation and drying.

In a preferable example of incorporating the filler, a rubber composition prepared by incorporating 0 to 150 parts by weight of silica in 100 parts by weight of the conjugated diene rubber (A) and a rubber composition prepared by incorporating 0 to 150 parts by weight of carbon black in 100 parts by weight of the conjugated diene rubber (B) are mixed together.

Ingredients other than the above-recited ingredients can be incorporated in necessary amounts in the rubber composition of the present invention according to the conventional manner. Such ingredients include, for example, a crosslinking agent, a crosslinking accelerator, an accelerator activator, an antioxidant, an activator, a process oil, a plasticizer, a lubricant and other fillers.

The crosslinking agent includes, for example, sulfur such as powdery sulfur, precipitated sulfur, colloidal sulfur, insoluble sulfur and highly dispersible sulfur; sulfur halides such as sulfur monochloride and sulfur dichloride; organic peroxides such as dicumyl peroxide and di-tert-butyl peroxide; quinonedioximes such as p-quinonedioxime and p,p'-dibenzoylquinonedioxime; organic polyamine compounds such as triethylenetetramine, hexamethylenediamine carbamate and 4,4'-methylenebis-o-chloroaniline; and an alkylphenol resin having a methylol group. Of these, sulfur is preferable. Powdery sulfur is more preferable. These crosslinking agents may be used either alone or as a combination of at least two thereof.

The amount of crosslinking agent is preferably in the range of 0.1 to 15 parts by weight, more preferably 0.5 to 5 parts by weight, based on 100 parts by weight of the total rubbers.

As specific examples of the crosslinking accelerator, there can be mentioned sulfenamide crosslinking accelerators such as N-cyclohexyl-2-benzothiazylsulfenamide, N-t-butyl-2-benzothiazolsulfenamide, N-oxyethylene-2-benzothiazolsulfenamide, N-oxyethylene-2-benzothiazolesulfenamide, and N,N'-diisopropyl-2-benzothiazolsulfenamide; guanidine crosslinking accelerators such as diphenylguanidine, diorthotolylguanidine and orthotolylbiguanidine; thiourea crosslinking accelerators such as diethylthiourea; thiazole crosslinking accelerators such as 2-mercaptobenzothizole, dibenzothiazyl disulfide and 2-mercaptobenzothizole zinc salt; thiuram crosslinking accelerators such as tetramethylthiuram monosulfide and tetramethylthiuram disulfide; dithiocarbamic acid crosslinking accelerators such as sodium dimethyldithiocarbamate and zinc dimethyldithiocarbamate; and xanthogenic acid crosslinking accelerators such as sodium isopropylxanthogenate, zinc isopropylxanthogenate and zinc butylxanthogenate. Of these, sulfenamide crosslinking accelerators are preferable. These crosslinking accelerators may be used either alone or as a combination of at least two thereof.

The amount of crosslinking accelerator is preferably in the range of 0.1 to 15 parts by weight, more preferably 0.5 to 5 parts by weight, based on 100 parts by weight of the total rubbers.

The accelerator activator includes, for example, higher fatty acids such as stearic acid, and zinc oxide. The zinc oxide preferably includes those having high surface activity which have a particle diameter of not larger than 5 μm, and, as specific examples of such zinc oxide, there can be mentioned activated zinc oxide having a particle diameter in the range of 0.05 to 0.2 μm and zinc oxide having a particle diameter in the range of 0.3 to 1 μm. Zinc oxide having been surface-treated with an amine dispersing agent or a wetting agent can also be used.

The amount of accelerator activator may be appropriately chosen, but the amount of higher fatty acids is preferably in the range of 0.05 to 15 parts by weight, more preferably 0.5 to 5 parts by weight, based on 100 parts by weight of the total rubbers, and the amount of zinc oxide is preferably in the range of 0.05 to 10 parts by weight, more preferably 0.5 to 3 parts by weight, based on 100 parts by weight of the total rubbers.

The process oil includes those which are conventionally used in rubber industry, and, as specific examples thereof, there can be mentioned paraffinic, aromatic and naphthenic petroleum softeners, vegetable softeners and fatty acids. As the petroleum softeners, those which have a polyaromatic content of smaller than 3% are preferable. The polyaromatic content is measured by the IP 346 method (testing method according to the Instutute Petroleum, United Kingdom).

As specific examples of the other ingredients, there can be mentioned active agents such as diethylene glycol, polyethylene glycol and silicone oil; fillers such as calcium carbonate, talc, clay, aluminum hydroxide and cornstarch; tackifiers such as petroleum resin and coumarone resin; and wax.

The conjugated diene rubber composition of the present invention can be prepared by kneading together the ingredients by a conventional procedure. For example, the conjugated diene rubber composition can be prepared by a procedure wherein rubber and ingredients, other than a crosslinking agent and a crosslinking accelerator, are kneaded together, and then, a crosslinking agent and a crosslinking accelerator are incorporated in the kneaded rubber. The kneading of rubber and ingredients other than a crosslinking agent and a crosslinking accelerator is carried out preferably at a temperature in the range of 80 to 200° C., more preferably 120 to 180° C., preferably for 30 seconds to 30 minutes. The incorporation of a crosslinking agent and a crosslinking accelerator are carried out after the kneaded rubber is cooled usually to a temperature not higher than 100° C., preferably not higher than 80° C.

The conjugated diene rubber composition of the present invention is usually used as a crosslinked vulcanizate. The crosslinking procedure is not particularly limited, and can appropriately be chosen depending upon the shape and size of a rubber vulcanizate. A rubber composition having a crosslinking agent incorporated therein is filled in a mold where the composition is heated whereby molding and crosslinking can be simultaneously conducted. Alternatively, a rubber composition having a crosslinking agent incorporated therein is first molded and then heated to be thereby crosslinked. The crosslinking is carried out preferably at a temperature in the range of 120 to 200° C., more preferably 140 to 180° C. The crosslinking time is usually about 1 to 120 minutes.

The conjugated diene rubber composition according to the present invention gives a rubber vulcanizate exhibiting sufficiently reduced heat build up, enhanced wet-grip property and high abrasion resistance. Therefore, the rubber vulcanizate can be used in various fields where such beneficial properties are desired. Thus, it is used as parts of tire such as tread, carcass, sidewall, inner-liner and bead; rubber articles such as hose, belt, shoe sole, vibration insulator rubber and automobile parts; and high-impact polystyrene, and resin-reinforcing rubber such as ABS resin. The rubber vulcanizate is especially useful as tread material for a low-fuel-consumption tire.

EXAMPLES

The invention will now be described by the following examples and comparative examples. Parts and % in the examples and comparative examples are by weight unless otherwise specified.

The physical properties were determined by the following methods.

(1) The bound styrene content in the conjugated diene rubber and the vinyl bond content in the 1,3-butadiene units were measured according to $^1$H-NMR, (2) The content of a branched conjugated diene polymer was determined by measuring the amount of the conjugated diene polymer before the reaction with a polyorganosiloxane, and measuring the amount of the finally obtained conjugated diene polymer. The measurement was carried out according to gel permeation chromatography under the following conditions.

Measurement apparatus: HLC-8020 (available from Tosoh Corporation)

Column: GMH-HR-H (available from Tosoh Corporation, two columns connected in series)

Detector: Differential refractometer (available from Tosoh Corporation)

Eluate: Tetrahydrofuran

Column temperature: 40° C.

From the thus-obtained analysis chart, weight fraction (a) of polymers having a molecular weight three times the molecular weight peak of conjugated diene polymer before the reaction with polyorganosiloxane, and weight fraction (b) of polymers having a molecular weight four times or more the molecular weight peak of conjugated diene polymer before the reaction with polyorganosiloxane were measured. The weight fraction (a) per the total amount of the finally obtained conjugated diene rubber is the amount (%) of 3-branched polymer, and the weight fraction (b) per the total amount of the finally obtained conjugated diene rubber is the amount (%) of 4- and more-branched polymers. The amount (%) of the 3- and more-branched polymers is the sum of the amount of 3-branched polymer and the amount of 4- and more-branched polymers.

(3-1) The weight average molecular weight of a conjugated diene polymer was determined under the same conditions as mentioned above according to gel permeation chromatography.

(3-2) The Mooney viscosity ($ML_{1+4}$, 100° C.) was measured according to JIS K6300

(4) Processability of a vulcanizable rubber composition was evaluated by the following standards.

(4-1) The shape of a rubber composition taken-out after the Banbury kneading was evaluated and expressed by the marks given according to the following four ratings.

Mark 1 Many fine and large lumps are found

Mark 2 A large lump and several fine lumps are found

Mark 3 A large mass is formed

Mark 4 Good-looking uniform large mass is formed (4-2) When the rubber composition was kneaded by the roll, the capability of rubber composition being wound round a roll was evaluated according to the following four ratings.

Mark 1 Rubber composition is difficult to wind round a roll

Mark 2 Rubber composition is wound round a roll with some difficulty

Mark 3 Rubber composition is wound round a roll

Mark 4 Rubber composition is easily wound round a roll (4-3) When the rubber composition was kneaded by the roll, the state of rubber composition wound round a roll was evaluated according to the following four ratings.

Mark 1 A large hole is formed

Mark 2 Small hole is formed

Mark 3 Sometimes small hole is formed

Mark 4 Rubber composition uniformly covers the roll (4-4) When the rubber composition was taken out in a sheet form from the roll, the surface state of sheet was evaluated according to the following four ratings.

Mark 1 Largely rugged

Mark 2 Slightly rugged

Mark 3 Approximately flat and smooth

Mark 4 Flat, smooth and lustrous

The total number of marks was made up, and the processability of rubber composition was expressed by the following five ratings, Mark 1 through Mark 5. The larger the mark number, the better the processability of a vulcanizable rubber composition.

Mark 1 Total number of marks 4 or 5
Mark 2 Total number of marks 6 to 8
Mark 3 Total number of marks 9 or 10
Mark 4 Total number of marks 11 to 13
Mark 5 Total number of marks 14 to 16

(5) Low heat build up was evaluated by tan δ as measured by RDA-II available from Reometrios Co., Ltd., at a twist of 4%, a frequency of 1 Hz and a temperature of 60° C. The tan δ was expressed by an index as that of Comparative Example being 100. The smaller the index, the better the low heat build up.

(6) Wet-grip property was evaluated by tan δ as measured by RDA-II available from Reometrics Co., Ltd., at a twist of 0.5%, a frequency of 20 Hz and a temperature of 0° C. The tan δ was expressed by an index as that of Comparative Example being 100. The larger the index, the better the wet-grip property.

(7) Abrasion resistance was measured by a Lambourn abrasion tester according to JIS K6264. The abrasion resistance was expressed by an index as that of Comparative Example being 100. The larger the index, the better the abrasion resistance.

(8) Tensile strength was evaluated by a tensile test according to JIS K6301. The stress at 300% elongation was measured and the tensile stress was expressed by an index as the tensile stress of Comparative Example being 100. The larger the index, the higher the tensile strength.

Example 1

(Production of Conjugated Diene Rubber Composition i)

An autoclave equipped with a stirrer was charged with 4,000 g of cyclohexane, 162 g of styrene, 438 g of 1,3-butadiene and 5.0 milli-moles of tetramethylethylenediamine. Then 8.7 milli-moles of n-butyllithium was added to the content to initiate a polymerization at 50° C. This amount of n-butyllithium corresponded to the sum of a catalyst amount required for the reaction with impurities which do not participate the polymerization reaction, and a catalyst amount required for polymerization reaction. When 10 minutes elapsed from the commencement of polymerization, a mixture of 40 g of styrene and 360 g of 1,3-butadiene was continuously added over a period of 60 minutes. The highest temperature during polymerization was 65° C.

After completion of the addition of styrene/1,3-butadiene mixture, the polymerization was continued further for 20 minutes. Then 312 g of 1,3-butadiene was added and the polymerization was further continued for 10 minutes. After confirmation of the fact that the polymerization conversion reached 100%, a small portion of the polymerization liquid was taken out as a sample. Excess methanol was added to the sample to stop the reaction. The polymerization liquid was then air-dried to obtain a polymer as a testing specimen for gel permeation chromatography.

Immediately after taking out the small portion of the polymerization liquid, a 10% solution in xylene of 2.3 milli-moles of 4,4'-bis(diethylamino)benzophenone (EAB) was added to the polymerization liquid and a reaction was conducted for 15 minutes. Then a 10% solution of polyorganosiloxane A in xylene was added and a reaction was conducted for 15 minutes. The amount of polyorganosiloxane A added was 0.015 times by mole the amount of n-butyllithium used for the copolymerization of 1,3-butadiene and styrene. Then methanol in an amount of twice by mole the amount of n-butyllithium used for copolymerization was added to stop the reaction whereby a polymerization liquid containing a conjugated diene rubber (A) and a conjugated diene rubber (B) was obtained. The conjugated diene rubber (A) and the conjugated diene rubber (B) according to the present invention are hereinafter abbreviated to as "polymer (A)" and "polymer (B)", respectively, when appropriate.

To the polymerization liquid, 0.1 part of Irganox 1520 (antioxidant, available from Ciba-Geigy Co.) per 100 parts of rubber was incorporated. Polymerization medium was removed by steam stripping, and the polymerization liquid was dried under vacuum to give a solid conjugated diene rubber composition i. The conjugated diene rubber composition I was analyzed and the results are shown in Table 1. The analyzed results of polymer (A) according to gel permeation chromatography (hereinafter abbreviated to as "GPC") were determined by deducting the analyzed results of polymer (B) by GPC from the analyzed results of the finally obtained polymer composition by GPC.

(Production of Conjugated Diene Rubber Composition I)

In a 250 ml Brabender mixer, 100 parts of the conjugated diene rubber composition i was masticated for 30 seconds. Then 30 parts of silica (Zeosil 1165MP available from Rhodia Co.) and 2.4 parts of a silane-coupling agent (Si69 available from Degussa Co.) were incorporated in the rubber composition. The mixture was kneaded for 1.5 minutes at an initiation temperature of 110° C., and then, 10 parts of process oil (Enerthene 1849A, available from British Petroleum Co.), 20 parts of carbon black (Seast KH available from Tokai Carbon Co.), 3 parts of zinc oxide, 2 parts of stearic acid and 2 parts of antioxidant (Nocrac 6C available from Ouchi Shinko Kagaku K.K.) were added. Then the mixture was further kneaded for 2 minutes, and the kneaded rubber mixture was taken out from the mixer. The temperature of the kneaded rubber mixture was 150° C. at the completion of kneading.

The kneaded rubber mixture was cooled to room temperature, and again kneaded by a Bravender mixer at an initiation temperature of 110° C. for 2 minutes and then taken out from the mixer.

Using an open roll, the above-mentioned kneaded mixture was kneaded at 50° C. together with 1.5 parts of sulfur and a crosslinking accelerator (mixture of 1.5 parts of N-cyclohexyl-2-benzothiazylsulfenamide and 0.5 part of diphenylguanidine) to give a sheet-form conjugated diene rubber composition I.

Processability of the conjugated diene rubber composition I was evaluated. The results are shown in Table 2.

The conjugated diene rubber composition was press-cured at 160° C. for 30 minutes to prepare a specimen. Low heat build up, wet-grip property and abrasion resistance of the specimen were measured. The results are shown in Table 2 wherein the results are expressed in terms of index as the results of Comparative Example 1 being 100.

Example 2

(Production of Conjugated Diene Rubber Composition ii and Conjugated Diene Rubber Composition II)

A conjugated diene rubber composition ii was prepared by substantially the same procedures and conditions as adopted in Example 1 except that 0.3 milli-moles of tin tetrachloride was used instead of 4,4'-bis(diethylamino)benzophenone (EAB). Analyzed results of the conjugated diene rubber composition ii are shown in Table 1.

A conjugated diene rubber composition II was prepared by incorporating ingredients in the conjugated diene rubber composition ii by substantially the same procedures and conditions as adopted in Example 1. Processability of the conjugated diene rubber composition II and properties of a rubber vulcanizate of the rubber composition II were evaluated. The results are shown in Table 2.

Comparative Example 1

(Production of Conjugated Diene Rubber Composition iii and Conjugated Diene Rubber Composition III)

A solid conjugated diene rubber composition iii was prepared by substantially the same procedures and conditions as adopted in Example 1 except that the amount of polyorganosiloxane was varied to 0.5 times by mole the amount of n-butyllithium used for the copolymerization of 1,3-butadiene and styrene. Analyzed results of the conjugated diene rubber composition iii are shown in Table 1.

A conjugated diene rubber composition III was prepared by incorporating ingredients in the conjugated diene rubber composition iii by substantially the same procedures and conditions as adopted in Example 1. Processability of the conjugated diene rubber composition III and properties of a rubber vulcanizate of the rubber composition III were evaluated. The results are shown in Table 2.

Comparative Example 2

(Production of Conjugated Diene Rubber Composition iv and Conjugated Diene Rubber Composition IV)

A solid conjugated diene rubber composition iv was prepared by substantially the same procedures and conditions as adopted in Example 1 except that EAB was not added, and tetramethoxysilane was used instead of polyorganosiloxane, and its amount was varied to 0.3 times by mole the amount of n-butyllithium used for the copolymerization of 1,3-butadiene and styrene. Analyzed results of the conjugated diene rubber composition iv are shown in Table 1.

A conjugated diene rubber composition IV was prepared by incorporating ingredients in the conjugated diene rubber composition iv by substantially the same procedures and conditions as adopted in Example 1. Processability of the conjugated diene rubber composition IV and properties of a rubber vulcanizate of the rubber composition IV were evaluated. The results are shown in Table 2.

Comparative Example 3

(Production of Conjugated Diane Rubber Composition v and Conjugated Diene Rubber Composition V)

A solid conjugated diene rubber composition v was prepared by substantially the same procedures and conditions as adopted in Example 1 except that methanol was used instead of EAR. Analyzed results of the conjugated diene rubber composition iv are shown in Table 1.

A conjugated diene rubber composition V was prepared by incorporating ingredients in the conjugated diene rubber composition v by substantially the same procedures and conditions as adopted in Example 1. Processability of the conjugated diene rubber composition V and properties of a rubber vulcanizate of the rubber composition V were evaluated. The results are shown in Table 2.

TABLE 1

|  | Examples | | Comparative Examples | | |
| --- | --- | --- | --- | --- | --- |
|  | 1 | 2 | 1 | 2 | 3 |
| Polymer (A) | | | | | |
| Polyorganosiloxane | A | A | A | — | A |
| Amount of polyorganosiloxane (moles/mole of n-butyllithium) | 0.015 | 0.015 | 0.5 | — | 0.015 |
| Amount of silane compound (moles/mole of n-butyllithium) | — | — | — | 0.3 | — |
| Polymer (B) | | | | | |
| Reactant compound | EAB *1 | SnCl$_2$ | EAB | — | MeOH |
| Conjugated diene rubber composition | i | ii | iii | iv | v |
| Peak molecular weight before reaction | 250,000 | 250,000 | 250,000 | 250,000 | 250,000 |
| Mw (weight average molecular weight) | 370,000 | 430,000 | 250,000 | 510,000 | 430,000 |
| Mw of polymer (A) | 1,020,000 | 990,000 | 1,060,000 | 800,000 | 1,000,000 |
| Mw of polymer (B) | 220,000 | 820,000 | 220,000 | — | 220,000 |
| Styrene unit content (%) | 20 | 20 | 20 | 20 | 20 |
| Vinyl bond content (%) | 55 | 55 | 55 | 55 | 55 |
| Amt of 3-branched polymer (%) | 7 | 6 | 2 | 30 | 11 |
| Amt of ≧4-branched polymers (%) *2 | 4 | 3 | 1 | 10 | 5 |
| Amt of ≧3-branched polymers (%) *3 | 11 | 9 | 3 | 40 | 16 |

Note,
*1 EAB: 4,4'-bis(diethylamino)benzophenone
*2 Amount of 4- and more-branched polymers
*3 Amount of 3- and more-branched polymers

TABLE 2

| Properties of Rubber | Examples | | Comparative Examples | | |
|---|---|---|---|---|---|
| | 1 | 2 | 1 | 2 | 3 |
| Composition | Conjugated diene rubber composition | | | | |
| | I | II | III | IV | V |
| Processability of crosslinkable rubber composition (marks) | 5 | 5 | 3 | 4 | 5 |
| Low heat build up (index) | 67 | 72 | 100 | 114 | 92 |
| Wet-grip property (index) | 119 | 118 | 100 | 89 | 103 |
| Abrasion resistance (index) | 131 | 133 | 100 | 93 | 104 |
| Tensile strength (index) | 135 | 130 | 100 | 89 | 102 |

Note,
Rubber ingredient in rubber compositon I is rubber composition i
Rubber ingredient in rubber compositon II is rubber composition ii
Rubber ingredient in rubber compositon III is rubber composition iii
Rubber ingredient in rubber compositon IV is rubber composition iv
Rubber ingredient in rubber compositon V is rubber composition v Example 3

(Production of Conjugated Diene Rubber Composition vi-1)

An autoclave equipped with a stirrer was charged with 4,000 g of cyclohexane, 171 g of styrene, 429 g of 1,3-butadiene and 6.5 milli-moles of tetramethylethylenediamine. Then 8.3 milli-moles of n-butyllithium was added to the content to initiate a polymerization at 40° C. This amount of n-butyllithium corresponded to the sum of a catalyst amount required for the reaction with impurities which do not participate the polymerization reaction, and a catalyst amount required for polymerization reaction. When 10 minutes elapsed from the commencement of polymerization, a mixture of 40 g of styrene and 360 g of 1,3-butadiene was continuously added over a period of 60 minutes. The highest temperature during polymerization was 60° C.

After completion of the addition of styrene/1,3-butadiene mixture, the polymerization was continued further for 20 minutes. After confirmation of the fact that the polymerization conversion reached 100%, a small portion of the polymerization liquid was taken out as a sample in the same manner as in Example 1. Excess methanol was added to the sample to stop the reaction. The polymerization liquid was then air-dried to obtain a polymer as a testing specimen for gel permeation chromatography.

Immediately after taking out the small portion of the polymerization liquid, a 10% solution of polyorganosiloxane B in xylene was added and a reaction was conducted for 15 minutes. The amount of polyorganosiloxane B added was 0.02 times by mole the amount of n-butyllithium used for the copolymerization of 1,3-butadiene and styrene. Then methanol in an amount of twice by mole the amount of n-butyllithium used for copolymerization was added to stop the reaction whereby a polymerization liquid containing a conjugated diene rubber vi-1 was obtained. A small portion of the polymerization liquid was taken out as a sample. The sample of polymerization liquid was air-dried to obtain a polymer as a testing specimen for gel permeation chromatography. Analyzed results of the specimen of conjugated diene rubber vi-1 are shown in Table 3.

(Production of Conjugated Diene Rubber Composition vi-2)

An autoclave equipped with a stirrer was charged with 4,000 g of cyclohexane, 196 g of styrene, 404 g of 1,3-butadiene and 2.2 milli-mole of tetramethylethylenediamine. Then 9.3 milli-moles of n-butyllithium was added to the content to initiate a polymerization at 45° C. This amount of n-butyllithium corresponded to the sum of a catalyst amount required for the reaction with impurities which do not participate the polymerization reaction, and a catalyst amount required for polymerization reaction. When 10 minutes elapsed from the commencement of polymerization, a mixture of 40 g of styrene and 360 g of 1,3-butadiene was continuously added over a period of 50 minutes. The highest temperature during polymerization was 75° C.

After completion of the addition of styrene/1,3-butadiene mixture, the polymerization was continued further for 20 minutes. Then 312 g of 1,3-butadiene was added and the polymerization was further continued for 10 minutes. After confirmation of the fact that the polymerization conversion reached 100%, a 10% solution of 7.5 milli-moles of N-methylpyrrolidone (NMP) in cyclojexane was added and a reaction was conducted for 15 minutes. Then methanol in an amount of twice by mole the amount of n-butyllithium used for copolymerization was added to stop the reaction whereby a polymerization liquid containing a conjugated diene rubber vi-2 was obtained. A small portion of the polymerization liquid was taken out as a sample and analyzed. Analyzed results of the specimen of conjugated diene rubber vi-2 are shown in Table 3.

(Production of Conjugated Diene Rubber Composition vi and Conjugated Diene Rubber Composition VI)

The polymerization liquid containing the conjugated diene rubber vi-1 and the polymerization liquid containing the conjugated diene rubber vi-2 were mixed together so that the ratio of the conjugated diene rubber vi-1 to the conjugated diene rubber v-ii is 2/1. The mixing was conducted for 30 minutes under stirring to give a polymer solution vi.

From the polymer solution vi, a solid conjugated diene rubber composition vi was prepared by the same procedures as in Example 1.

In a 250 ml Brabender mixer, 85 parts of the conjugated diene rubber composition vi and 15 parts of high-cis polybutadiene rubber (Nipol BR1220N available form Zeon Corporation) were masticated together for 30 seconds. Then 45 parts of silica (Nipsil AQ available from Tosoh Silica Corporation) and 4.5 parts of a silane-coupling agent (S169) were incorporated in the masticated rubber composition. The mixture was kneaded for 1.5 minutes at an initiation temperature of 110° C., and then, 15 parts of process oil (Enerthene 1849A), 20 parts of carbon black (Seast 6 available from Tokai Carbon Co.), 3 parts of zinc oxide, 2 parts of stearic acid and 2 parts of antioxidant (Nocrac 6C) were added. Then the mixture was further kneaded for 2 minutes, and the kneaded rubber mixture was taken out from the mixer. The temperature of the kneaded rubber mixture was 150° C. at the completion of kneading.

The kneaded rubber mixture was cooled to room temperature, and again kneaded by a Bravender mixer at an initiation temperature of 110° C. for 2 minutes and then taken out from the mixer.

Using an open roll, the above-mentioned kneaded mixture was kneaded at 50° C. together with 1.5 parts of sulfur and a crosslinking accelerator (mixture of 1.5 parts of N-cyclohexyl-2-benzothiazylsulfenamide and 0.9 part of diphenylguanidine) to give a sheet-form conjugated diene rubber composition VI.

Processability of the conjugated diene rubber composition VI was evaluated. The results are shown in Table 4.

The conjugated diene rubber composition was press-cured at 160° C. for 30 minutes to prepare a specimen. Properties of the specimen were measured by the same methods as in Example 1. The results are shown in Table 4 wherein the results are expressed in terms of index as the results of Comparative Example 4 being 100.

Comparative Example 4

(Production of Conjugated Diene Rubber vi-3 and Conjugated Diene Rubber vi-4)

A conjugated diene rubber vi-3 was produced by substantially the same procedures and conditions as adopted for the production of the conjugated diene rubber vi-1 in Example 3 except that the amount of polyorganosiloxane was varied to 0.5 times by mole the amount of n-butyllithium used for the copolymerization of 1,3-butadiene and styrene.

A conjugated diene rubber vi-4 was produced by substantially the same procedures and conditions as adopted for the production of the conjugated diene rubber vi-2 in Example 3 except that methanol was used instead of NMP.

The conjugated diene rubber vi-3 and the conjugated diene rubber vi-4 were analyzed. The results are shown in Table 3.

(Production of Conjugated Diene Rubber Composition vii and Conjugated Diene Rubber Composition VII)

From the conjugated diene rubber vi-3 and the conjugated diene rubber vi-4, a solid conjugated diene rubber composition vii was prepared through a polymer solution vii substantially the same procedures and conditions as adopted for the production of a solid conjugated diene rubber composition vi through the polymer solution vi in Example 3.

A conjugated diene rubber composition VII was prepared by incorporating ingredients in the conjugated dione rubber composition vii by substantially the same procedures and conditions as adopted in Example 1. Processability of the conjugated diene rubber composition VII and properties of a rubber vulcanizate of the rubber composition VII were evaluated. The results are shown in Table 4.

TABLE 4

|  | Example 3 | Comparative Example 4 |
|---|---|---|
|  | Conjugated diene rubber composition | |
| Properties of Rubber Composition | VI | VII |
| Processability of crosslinkable rubber composition (marks) | 5 | 2 |
| Low heat build up (index) | 60 | 100 |
| Wet-grip property (index) | 119 | 100 |
| Abrasion resistance (index) | 148 | 100 |
| Tensile strength (index) | 191 | 100 |

Note,
rubber ingredient in rubber composition VI is rubber composition vi (conjugated diene rubber vi-1 + conjugated diene rubber vi-2) + high-cis polybutadiene rubber Example 4

(Production of Conjugated Diene Rubber viii-1)

An autoclave equipped with a stirrer was charged with 4,000 g of cyclohexane, 120 g of styrene, 380 g of 1,3-butadiene and 4.5 milli-moles of tetramethylethylenediamine. Then 8.6 milli-moles of n-butyllithium was added to the content to initiate a polymerization at 50° C. This amount of n-butyllithium corresponded to the sum of a catalyst amount required for the reaction with impurities which do not participate the polymerization reaction, and a catalyst amount required for polymerization reaction. When 10 minutes elapsed from the commencement of polymerization, a mixture of 50 g of styrene and 450 g of 1,3-butadiene was continuously added over a period of 60 minutes. The highest temperature during polymerization was 70° C.

After completion of the addition of styrene/1,3-butadiene mixture, the polymerization was continued further for 15

TABLE 3

|  | Example 3 | | Comparative Example 4 | |
|---|---|---|---|---|
| Polymer (A) | | | | |
| Polyorganosiloxane | B | — | B | — |
| Amount of polyorganosiloxane (moles/mole of n-butyllithium) | 0.02 | — | 0.5 | — |
| Amount of silane compound (moles/mole of n-butyllithium) | — | — | — | — |
| Polymer (B) | | | | |
| Reactant compound | | NMP *1 | — | MeOH |
| Conjugated diene rubber composition | vi-1 | vi-2 | vi-3 | vi-4 |
| Peak molecular weight before reaction | 250,000 | 240,000 | 250,000 | 240,000 |
| Mw (weight average molecular weight) | 560,000 | 210,000 | 300,000 | 210,000 |
| Mw of polymer (A) | 1,070,000 | — | 970,000 | — |
| Mw of polymer (B) | — | 210,000 | — | 210,000 |
| Styrene unit content (%) | 21 | 23.5 | 21 | 23.5 |
| Vinyl bond content (%) | 63 | 33 | 63 | 33 |
| Amt of 3-branched polymer (%) | 20 | — | 1 | — |
| Amt of ≧4-branched polymers (%) *2 | 13 | — | 1 | — |
| Amt of ≧3-branched polymers (%) *3 | 33 | — | 2 | — |

Note,
*1 NMP: N-methylpyrrolidone
*2 Amount of 4- and more-branched polymers
*3 Amount of 3- and more-branched polymers minutes. After confirmation of the fact that the polymerization conversion reached 100%, a small portion of the polymerization liquid was taken out and a testing specimen for gel permeation chromatography analysis was prepared in the same manner as in Example 1.

Immediately after taking out the small portion of the polymerization liquid, a 10% solution of polyorganosiloxane C in xylene was added and a reaction was conducted for 15 minutes. The amount of polyorganosiloxane C added was 0.03 times by mole the amount of n-butyllithium used for the copolymerization of 1,3-butadiene and styrene. Then methanol in an amount of twice by mole the amount of n-butyllithium used for copolymerization was added to stop the reaction whereby a polymer solution containing a conjugated diene rubber viii-1 was obtained.

From the polymer solution containing a conjugated diene rubber viii-1, a solid conjugated diene rubber viii-1 was obtained by substantially the same procedures and conditions as in Example 1. The solid conjugated diene rubber viii-1 was analyzed, and the results are shown in Table 5.

(Production of Conjugated Diene Rubber viii-2)

An autoclave equipped with a stirrer was charged with 4,000 g of cyclohexane, 171 g of styrene, 429 g of 1,3-butadiene and 8.0 milli-moles of tetramethylethylenediamine. Then 8.6 milli-moles of n-butyllithium was added to the content to initiate a polymerization at 40° C. This amount of n-butyllithium corresponded to the sum of a catalyst amount required for the reaction with impurities which do not participate the polymerization reaction, and a catalyst amount required for polymerization reaction. When 10 minutes elapsed from the commencement of polymerization, a mixture of 40 g of styrene and 360 g of 1,3-butadiene was continuously added over a period of 60 minutes. The highest temperature during polymerization was 60° C.

After completion of the addition of styrene/1,3-butadiene mixture, the polymerization was continued further for 20 minutes. Then 12 g of 1,3-butadiene was added and the polymerization was further continued for 10 minutes. After confirmation of the fact that the polymerization conversion reached 100%, a 20% solution of 0.6 milli-mole of tin tetrachloride in cyclohexane was added, and a reaction was conducted for 15 minutes. Then a 10% solution of 4.3 milli-moles of N-methylpyrrolidone (NMP) in cyclohexane was added and a reaction was conducted for 15 minutes. Then methanol in an amount of twice by mole the amount of n-butyllithium used for copolymerization was added to stop the reaction whereby a polymer solution containing a conjugated diene rubber viii-2 was obtained.

From the polymer solution containing a conjugated diene rubber viii-2, a solid conjugated diene rubber viii-2 was obtained by substantially the same procedures and conditions as in Example 1. The solid conjugated diene rubber viii-2 was analyzed, and the results are shown in Table 5.

(Production of Conjugated Diene Rubber Composition VIII)

In a 250 ml Brabender mixer, 35 parts of the conjugated diene rubber composition viii-1, 35 parts of the conjugated diene rubber composition viii-2, and 30 parts of natural rubber were masticated together for 30 seconds. Then 30 parts of silica (Zeosil 1135MP available from Rhodia Co.) and 1.9 parts of a silane-coupling agent (S169) were incorporated in the masticated rubber composition. The mixture was kneaded for 1.5 minutes at an initiation temperature of 110° C., and then, 10 parts of process oil (Enerthene 1849A), 30 parts of carbon black (Seast 7HM available from Tokai Carbon Co.), 3 parts of zinc oxide, 2 parts of stearic acid and 2 parts of antioxidant (Nocrac 6C) were added. Then the mixture was further kneaded for 2 minutes, and the kneaded rubber mixture was taken out from the mixer. The temperature of the kneaded rubber mixture was 150° C. at the completion of kneading.

The kneaded rubber mixture was cooled to room temperature, and again kneaded by a Bravender mixer at an initiation temperature of 110° C. for 2 minutes and then taken out from the mixer.

Using an open roll, the above-mentioned kneaded mixture was kneaded at 50° C. together with 1.5 parts of sulfur and a crosslinking accelerator (mixture of 1.5 parts of N-cyclohexyl-2-benzothiazylsulfenamide and 0.4 part of diphenylguanidine) to give a sheet-form conjugated diene rubber composition VIII.

Processability of the conjugated diene rubber composition VIII was evaluated. The results are shown in Table 6.

The conjugated diene rubber composition was press-cured at 160° C. for 30 minutes to prepare a specimen. Properties of the specimen were measured. The results are shown in Table 6 wherein the results are expressed in terms of index as the results of Comparative Example 6 being 100.

Comparative Example 5

(Production of Conjugated Diene Rubber viii-3)

A solid conjugated diene rubber viii-3 was produced by substantially the same procedures and conditions as adopted for the production of the conjugated diene rubber viii-1 in Example 4 except that, instead of polyorganosiloxane C, tetramethoxysilane was used in an amount 0.3 times by mole the amount of n-butyllithium used for the copolymerization of 1,3-butadiene and styrene. The conjugated diene rubber viii-3 was analyzed. The results are shown in Table 5.

(Production of Conjugated Diene Rubber Composition IX)

From the conjugated diene rubber viii-2 and the conjugated diene rubber viii-3, a solid conjugated diene rubber composition IX was prepared by substantially the same procedures and conditions as adopted in Example 4 except that the conjugated diene rubber viii-3 was used instead of the conjugated diene rubber viii-1. Processability of the conjugated diene rubber composition IX and properties of a rubber vulcanizate of the rubber composition IX were evaluated. The results are shown in Table 6.

TABLE 5

| | Production Examples | | |
|---|---|---|---|
| | viii-1 | viii-2 | viii-3 |
| Polymer (A) | | | |
| Polyorganosiloxane | C | — | — |
| Amount of polyorganosiloxane (moles/mole of n-butyllithium) | 0.03 | — | — |
| Amount of silane compound (moles/mole of n-butyllithium) | — | — | 0.3 |
| Polymer (B) | | | |
| Reactant compound | — | NPP *1, SnCl$_4$ | — |
| Conjugated diene rubber composition | | | |
| Peak molecular weight before reaction | 250,000 | 240,000 | 250,000 |
| Mw (weight average molecular weight) | 440,000 | 400,000 | 410,000 |
| Mw of polymer (A) | 920,000 | — | 800,000 |
| Mw of polymer (B) | — | 400,000 | — |
| Styrene unit content (%) | 17 | 21 | 17 |

TABLE 5-continued

|  | Production Examples | | |
| --- | --- | --- | --- |
|  | viii-1 | viii-2 | viii-3 |
| Vinyl bond content (%) | 45 | 63 | 45 |
| Amt of 3-branched polymer (%) | 13 | — | 22 |
| Amt of ≧4-branched polymers (%) *2 | 8 | — | 10 |
| Amt of ≧3-branched polymers (%) *3 | 21 | — | 32 |

Note,
*1 NPP: N-phenylpyrrolidone
*2 Amount of 4- and more-branched polymers
*3 Amount of 3- and more-branched polymers

TABLE 6

|  | Example 4 | Comparative Example 5 |
| --- | --- | --- |
|  | Conjugated diene rubber composition | |
| Properties of Rubber Composition | VIII | IX |
| Processability of crosslinkable rubber composition (marks) | 5 | 5 |
| Low heat build up (index) | 86 | 100 |
| Wet-grip property (index) | 108 | 100 |
| Abrasion resistance (index) | 111 | 100 |
| Tensile strength (index) | 115 | 100 |

Note,
Rubber ingredient in rubber composition VIII is conjugated diene rubber viii-1 + conjugated diene rubber viii-2 + natural rubber
Rubber ingredient in rubber composition IX is conjugated diene rubber viii-2 + conjugated diene rubber viii-3 + natural rubber Example 5

(Production of Conjugated Diene Rubber x-1)

An autoclave equipped with a stirrer was charged with 4,000 g of cyclohexane, 270 g of styrene, 300 g of 1,3-butadiene, 30 g of isoprene and 2.9 milli-moles of tetramethylethylenediamine. Then 5.7 milli-moles of n-butyllithium was added to the content to initiate a polymerization at 45° C. This amount of n-butyllithium corresponded to the sum of a catalyst amount required for the reaction with impurities which do not participate the polymerization reaction, and a catalyst amount required for polymerization reaction. When 20 minutes elapsed from the commencement of polymerization, a mixture of 80 g of styrene and 320 g of 1,3-butadiene was continuously added over a period of 60 minutes. The highest temperature during polymerization was 65° C.

After completion of the addition of styrene/1,3-butadiene mixture, the polymerization was continued further for 60 minutes. Then 8 g of isoprene was added and the reaction was further continued for 10 minutes. After confirmation of the fact that the polymerization conversion reached 100%, a small portion of the polymerization liquid was taken out and a testing specimen for gel permeation chromatography analysis was prepared in the same manner as in Example 1.

Immediately after taking out the small portion of the polymerization liquid, a 10% solution of polyorganosiloxane D in xylene was added and a reaction was conducted for 30 minutes. The amount of polyorganosiloxane D added was 0.02 times by mole the amount of n-butyllithium used for the copolymerization of 1,3-butadiene, styrene and isoprene. Then methanol in an amount of twice by mole the amount of n-butyllithium used for copolymerization was added to stop the reaction whereby a polymer solution containing a conjugated diene rubber x-1 was obtained.

From the polymer solution containing the conjugated diene rubber x-1, a solid conjugated diene rubber x-1 was obtained by substantially the same procedures and conditions as in Example 1. The solid conjugated diene rubber x-1 was analyzed, and the results are shown in Table 7.

To the above-mentioned polymer solution containing the conjugated diene rubber x-1, 0.14 part of antioxidant (Irganox 1520) and 37.5 parts of process oil (Enerthene 1849A), based on 100 parts of the conjugated diene rubber x-1, were added. Polymerization medium was removed by steam-stripping, and then the residue was vacuum-dried at 60° C. for 24 hours to give a solid conjugated diene rubber x-1.

(Production of Conjugated Diene Rubber x-2)

An autoclave equipped with a stirrer was charged with 4,000 g of cyclohexane, 8.6 milli-moles of tetramethylethylenediamine and 29.0 milli-moles of n-butyllithium. This amount of n-butyllithium corresponded to the sum of a catalyst amount required for the reaction with impurities which do not participate the polymerization reaction, and a catalyst amount required for polymerization reaction. Then 350 g of styrene and 650 g of 1,3-butadiene were continuously added to the content over a period of 90 minutes. A polymerization was initiated at 45° C. The highest temperature during polymerization was 50° C.

After completion of the continuous addition of styrene and 1,3-butadiene, the polymerization was continued further for 30 minutes. After confirmation of the fact that the polymerization conversion reached 100%, a small portion of the polymerization liquid was taken out and a testing specimen for gel permeation chromatography analysis was prepared in the same manner as in Example 1.

Immediately after taking out the small portion of the polymerization liquid, a 10% solution of polyorganosiloxane C in xylene was added and a reaction was conducted for 15 minutes. The amount of polyorganosiloxane C added was 0.08 times by mole the amount of n-butyllithium used for the copolymerization of 1,3-butadiene and styrene. Then methanol in an amount of 1.5 times by mole the amount of n-butyllithium used for copolymerization was added to stop the reaction whereby a polymer solution containing a conjugated diene rubber x-2 was obtained.

From the polymer solution containing the conjugated diene rubber x-2, a solid conjugated diene rubber x-2 was obtained by substantially the same procedures and conditions as in Example 1. The solid conjugated diene rubber x-2 was analyzed, and the results are shown in Table 7.

(Production of Conjugated Diene Rubber x-3)

An autoclave equipped with a stirrer was charged with 4,000 g of cyclohexane, 500 g of 1,3-butadiene and 0.2 milli-mole of tetramethylethylenediamine. Then 8.9 milli-moles of n-butyllithium was added to initiate a polymerization was initiated at 50° C. This amount of n-butyllithium corresponded to the sum of a catalyst amount required for the reaction with impurities which do not participate the polymerization reaction, and a catalyst amount required for polymerization reaction. When 20 minutes elapsed from the commencement of polymerization, 500 g of 1,3-butadiene was continuously added over a period of 30 minutes. The highest temperature during polymerization was 80° C.

After completion of the continuous addition of 1,3-butadiene, the polymerization was continued further for 20 minutes. After confirmation of the fact that the polymerization conversion reached 100%, a 20% solution of 0.7 milli-mole of tin tetrachloride in cyclohexane was added and a reaction was conducted for 15 minutes. Then a 10% solution of 4.5 milli-moles of N-methyl-ε-caprolactam (NMC) was added and a reaction was conducted for 15 minutes. Then methanol in an amount of twice by mole the amount of n-butyllithium used for polymerization was added to stop the reaction whereby a polymer solution containing a conjugated diene rubber x-3 was obtained.

From the polymer solution containing the conjugated diene rubber x-3, a solid conjugated diens rubber x-3 was obtained by substantially the same procedures and conditions as in Example 1. The solid conjugated diene rubber x-3 was analyzed, and the results are shown in Table 7.

(Production of Conjugated Diene Rubber Composition X)

In a 250 ml Brabender mixer, 110 parts of the conjugated diene rubber composition x-1 and 27.5 parts of emulsion polymerized SBR (Nipol 1712 available from Zeon Corporation) were masticated together for 30 seconds. Then 55 parts of silica (Zeosil 165GR available from Rhodia Co.) and 6.8 parts of a silane-coupling agent (S169) were incorporated in the masticated rubber composition. The mixture was kneaded for 1.5 minutes at an initiation temperature of 110° C., and then, 12.5 parts of process oil (Enerthene 1849A), 30.7 parts of silica (Zeosil 165GR), 2 parts of zinc oxide, 2 parts of stearic acid and 2 parts of antioxidant (Nocrac 6C) were added. Then the mixture was further kneaded for 2 minutes, and the kneaded rubber mixture (x-a) was taken out from the mixer. The temperature of the kneaded rubber mixture (x-a) was 150° C. at the completion of kneading.

Separately, in a 250 ml Brabender mixer, 67 parts of the conjugated diene rubber composition x-3 and 45.5 parts of emulsion polymerized SBR (Nipol 1712) were masticated together for 30 seconds. Then 66.7 parts of carbon black (Seast 7HM), 4 parts of process oil (Enerthene 1849A), 5 parts of zinc oxide, 2 parts of stearic acid and 2 parts of antioxidant (Nocrac 6C) were added in the masticated rubber composition. The mixture was kneaded for 2.5 minutes at an initiation temperature of 110° C. The kneaded rubber mixture (x-b) was taken out from the mixer. The temperature of the kneaded rubber mixture (x-b) was 150° C. at the completion of kneading.

The kneaded rubber mixtures (x-a) and (x-b) were cooled to room temperature. Then 174 parts of the kneaded rubber mixtures (x-a) and 57.7 parts of the kneaded rubber mixtures (x-b) were kneaded together by a Bravender mixer at an initiation temperature of 110° C. for 2 minutes, and then thus-obtained rubber mixture (x-c) was taken out from the mixer.

Using an open roll, the above-mentioned kneaded mixture (x-c) was kneaded at 50° C. together with 1.5 parts of sulfur and a crosslinking accelerator (mixture of 1.7 parts of N-cyclohexyl-2-benzothiazylsulfenamide and 1.5 parts of diphenylguanidine) to give a sheet-form conjugated diene rubber composition X.

Processability of the conjugated diene rubber composition X was evaluated. The results are shown in Table 8.

The conjugated diene rubber composition was press-cured at 160° C. for 30 minutes to prepare a specimen. Low heat build up, wet-grip property, abrasion resistance and tensile strength were measured. The results are shown in Table 8 wherein the results are expressed in terms of index as the results of Comparative Example 6 being 100.

Example 6

(Production of Conjugated Diene Rubber Composition XI)

The polymer solution containing the conjugated diene rubber x-1 and the polymer solution containing the conjugated diene rubber x-2 were mixed together so that the ratio of the amount of conjugated diene rubber x-1 to the amount of conjugated diene rubber x-2 is 4/1. The mixture was stirred for 30 minutes to give a polymer solution. To the polymer solution, 0.14 part of antioxidant (Irganox 1520) and 37.5 parts of process oil (Enerthene 1849A), both based on 100 parts of the rubber ingredients, were added. Polymerization medium was removed by steam-stripping. Then the residue was vacuum-dried at 60° C. for 24 hours to give a solid conjugated diene rubber composition XI.

(Production of Conjugated Diene Rubber Composition XII)

A conjugated diene rubber composition XII was produced by substantially the same kneading procedures and conditions as adopted in Example 5 wherein the solid conjugated diene rubber composition XI was used instead of the solid conjugated diene rubber x-1. The evaluation results of the conjugated diene rubber composition XII are shown in Table 8.

Comparative Example 6

Production of Conjugated Diene Rubber x-4)

A conjugated diene rubber x-4 was produced by substantially the same procedures and conditions as adopted for the production of the conjugated diene rubber x-1 in Example 5 wherein, instead of polyorganosiloxane, tetramethoxysilane was used in an amount of 0.3 times by mole the amount of n-butyllithium used for the copolymerization of 1,3-butadiene, styrene and isoprene.

A solid conjugated diene rubber x-4 was produced from the conjugated diene rubber x-4 in the same manner as that for the production of the solid conjugated diene rubber x-1 from the conjugated diene rubber x-1.

(Production of Conjugated Diene Rubber Composition XIII)

A conjugated diene rubber composition XIII was produced by substantially the same kneading procedures and conditions as adopted in Example 5 wherein the solid conjugated diene rubber x-4 was used instead of the solid conjugated diene rubber x-1, and low-cis polybutadiene rubber (Nipol BR1242 available from Zeon Corporation) was used instead of the conjugated diene rubber x-3. The evaluation results of the conjugated diene rubber composition XIII are shown in Table 8.

TABLE 7

|  | Production Examples | | | |
| --- | --- | --- | --- | --- |
|  | x-1 | x-2 | x-3 | x-4 |
| Polymer (A) | | | | |
| Polyorganosiloxane | D | O | — | — |
| Amount of polyorganosiloxane (moles/mole of n-butyllithium) | 0.02 | 0.008 | — | — |

TABLE 7-continued

| | Production Examples | | | |
|---|---|---|---|---|
| | x-1 | x-2 | x-3 | x-4 |
| Amount of silane compound (moles/mole of n-butyllithium) | — | — | — | 0.3 |
| Polymer (B) | | | | |
| Reactant compound | — | — | NMC *1, SnCl$_4$ | — |
| Conjugated diene rubber composition | | | | |
| Peak molecular weight before reaction | 400,000 | 60,000 | 250,000 | 250,000 |
| Mw (weight average molecular weight) | 960,000 | 140,000 | 410,000 | 730,000 |
| Mw of polymer (A) | 1,390,000 | 240,000 | — | 1,250,000 |
| Mw of polymer (B) | — | — | 410,000 | — |
| Styrene unit content (%) | 35 | 35 | 0 | 35 |
| Vinyl bond content (%) | 40 | 40 | 12 | 40 |
| Amt of 3-branched polymer (%) | 21 | 18 | — | 20 |
| Amt of ≧4-branched polymers (%) *2 | 17 | 10 | — | 5 |
| Amt of ≧3-branched polymers (%) *3 | 37 | 28 | — | 25 |

Note,
*1 NMC: N-methyl-ε-caprolactam
*2 Amount of 4- and more-branched polymers
*3 Amount of 3- and more-branched polymers

TABLE 8

| | Example 5 | Example 6 | Comparative Example 6 |
|---|---|---|---|
| | Conjugated diene rubber composition | | |
| Properties of Rubber Composition | X | XII | XIII |
| Processability of crosslinkable rubber composition (marks) | 5 | 5 | 4 |
| Low heat build up (index) | 86 | 73 | 100 |
| Wet-grip property (index) | 115 | 120 | 100 |
| Abrasion resistance (index) | 112 | 126 | 100 |
| Tensile strength (index) | 107 | 118 | 100 |

Note,
Rubber ingredient in rubber composition X is conjugated diene rubber x-1 + conjugated diene rubber x-3 + SBR
Rubber ingredient in rubber composition XII is conjugated diene rubber composition XI (conjugated diene x-1 + conjugated diene rubber x-2) + conjugated diene rubber x-3 + SBR
Rubber ingredient in rubber composition XIII is conjugated diene rubber x-4 + low-cis polybutadiene rubber + SBR)

Polyorganosiloxanes A through D as used in the above Examples and Comparative Examples are represented by the following formula (i.e., general formula (1) before reaction),

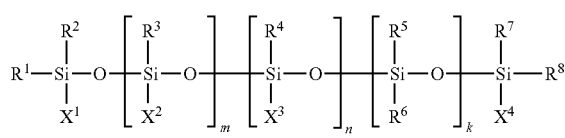

Polyorganosiloxane A (m=80, n=0, k=120)

X$^2$:

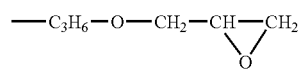

X$^1$, X$^4$, R$^1$~R$^3$, R$^6$~R$^8$: —CH$_3$

Polyorganosiloxane B (m=60, n=0, k=30)

X$^2$:

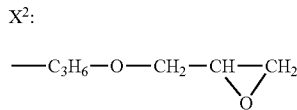

X$^1$, X$^4$, R$^1$~R$^3$, R$^5$~R$^8$: —CH$_3$

Polyorganosiloxane C (m=40, n=0, k=80)

X$^2$:

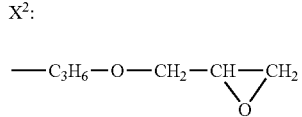

X$^1$, X$^4$, R$^1$~R$^3$, R$^5$~R$^8$: —CH$_3$

Polyorganosiloxane D (m=60, n=0, k=0)

X$^2$:

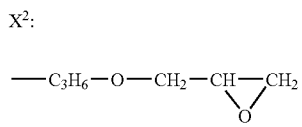

X$^1$, X$^4$, R$^1$~R$^3$, R$^7$, R$^8$: —CH$_3$

The following will be seen from the above-recited Examples and Comparative Examples.

In reference to Tables 1 and 2:

Comparative Example 1: Conjugated diene rubber composition III prepared by incorporating a large amount of polyorganosiloxane A contains a small amount of 3- and more-branched polymers. The vulcanizable rubber composition has poor processability, and the rubber vulcanizate exhibits a relatively large heat build up, and has poor wet-grip property, poor abrasion resistance and low tensile strength.

Comparative Example 2: Conjugated diene rubber composition IV prepared without reaction of a functional group-containing compound (EAB) and by using tetramethoxysilane instead of polyorganosiloxane contains a large amount of 3- and more-branched polymers. But, the vulcanizable rubber composition has poor processability, and the rubber vulcanizate exhibits a large heat build up, and has very poor wet-grip property, very poor abrasion resistance and very low tensile strength.

Comparative Example 3: Conjugated diene rubber composition V prepared by using methanol instead of a functional group-containing compound (EAB) contains a relatively large amount of 3- and more-branched polymers. The vulcanizable rubber composition has good processability, but the rubber vulcanizate exhibits a relatively large heat build up, and has poor wet-grip property, poor abrasion resistance and low tensile strength.

In contrast to these comparative examples, the conjugated diene rubber compositions I and II according to the present invention contain a relatively large amount of 3- and more-branched polymers. The vulcanizable rubber composition has good processability, and the rubber vulcanizate exhibits a sufficiently reduced heat build up, and has good wet-grip property and good abrasion resistance.

Alternatively, in the case when a conjugated diene polymer having reacted with polyorganosiloxane and a conjugated diene polymer having reacted with a functional group-containing compound (NMP, NPP, NMC or SnCl$_4$) are blended together, the vulcanizable rubber composition has good processability, and the rubber vulcanizate exhibits a sufficiently reduced heat build up, and has good wet-grip property and good abrasion resistance (as seen from comparison of Example 3 with Comparative Example in Tables 3 and 4; comparison of Example 4 with Comparative Example 5 in Tables 5 and 6; and comparison of Examples 5 and with Comparative Example 6 in Tables 7 and 8).

INDUSTRIAL APPLICABILITY

The conjugated diene rubber composition according to the present invention gives, when silica is incorporated therein, a vulcanizable rubber composition having improved processability and giving a rubber vulcanizate having well reduced heat build up, enhanced wet-grip property and high abrasion resistance.

Therefore, the rubber vulcanizate can be used in various fields where such beneficial properties are desired. Thus, it is used as, for example, parts of tire such as tread, carcass, sidewall, inner-liner and bead; rubber articles such as hose, belt, shoe sole, vibration insulator rubber and automobile parts; and high-impact polystyrene, and resin-reinforcing rubber such as ABS resin. The rubber vulcanizate is especially useful as tread material for a low-fuel-consumption tire.

The invention claimed is:

1. A conjugated diene rubber composition comprising:
(A) 5% to 95% by weight of a conjugated diene rubber having a weight average molecular weight in the range of 1,000 to 3,000,000 wherein at least three conjugated diene polymer chains in said rubber are bonded together through at least one polyorganosiloxane selected from those which are represented by the general formulae (1), (2) and (3), shown below:

General formula (1):

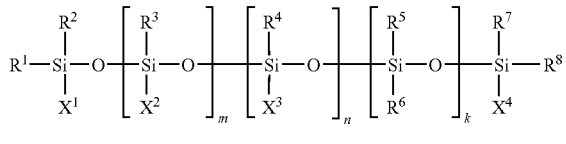

wherein
R$^1$ through R$^8$ represent an alkyl group having 1 to 6 carbon atoms or an aryl group having 6 to 12 carbon atoms, R$^1$ through R$^8$ being the same or different;
(i) a part of the sum of X$^1$ and X$^4$ is a functional group selected from the group consisting of a hydrocarbon group containing a 2-pyrrolidonyl group and an epoxy-containing group having 4 to 12 carbon atoms and the remainder of the sum of X$^1$ and X$^4$ is a group derived from said functional group by the reaction of said functional group with an active metal at a terminal of the active conjugated diene polymer chains, or (ii) a part of the sum of X$^1$ and X$^4$ is an alkoxyl group having 1 to 5 carbon atoms and the remainder of the sum of X$^1$ and X$^4$ is a single bond, or (iii) X$^1$ and X$^4$ are an alkyl group having 1 to 6 carbon atoms or an aryl group having 6 to 12 carbon atoms, X$^1$ and X$^4$ being the same or different;
(i) a part of X$^2$ is a functional group selected from the group consisting of a hydrocarbon group containing a 2-pyrrolidonyl group and an epoxy-containing group having 4 to 12 carbon atoms and the remainder of X$^2$ is a group derived from said functional group by the reaction of said functional group with an active metal at a terminal of the active conjugated diene polymer chains, or (ii) a part of X$^2$ is an alkoxyl group having 1 to 5 carbon atoms and the remainder of X$^2$ is a single bond;
X$^3$ is a group comprising 2 to 20 alkylene glycol repeating units, provided that a part of X$^3$ may be a group derived from the group comprising 2 to 20 alkylene glycol repeating units; and
m is an integer of 3 to 200, n is an integer of 0 to 200 and k is an integer of 0 to 200;

General formula (2):

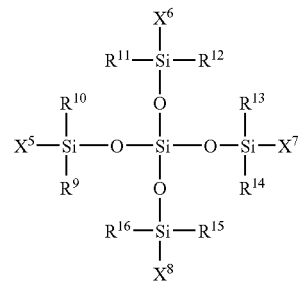

wherein
R$^9$ through R$^{16}$ represent an alkyl group having 1 to 6 carbon atoms or an aryl group having 6 to 12 carbon atoms, R$^9$ through R$^{16}$ being the same or different; and
(i) a part of the sum of X$^5$ through X$^8$ is a functional group selected from the group consisting of a hydrocarbon group containing a 2-pyrrolidonyl group and an epoxy-containing group having 4 to 12 carbon atoms and the remainder of the sum of $X^5$ through $X^8$ is a group derived from said functional group by the reaction of said functional group with an active metal at a terminal of the active conjugated diene polymer chains, or (ii) a part of the sum of $X^5$ through $X^8$ is an alkoxyl group having 1 to 5 carbon atoms and the remainder of the sum of $X^5$ through $X^8$ is a single bond;

General formula (3):

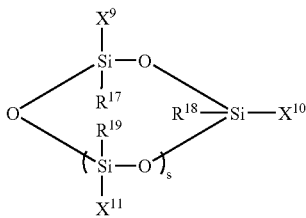

wherein
  $R^{17}$, $R^{18}$ and $R^{19}$ represent an alkyl group having 1 to 6 carbon atoms or an aryl group having 6 to 12 carbon atoms, $R^{17}$, $R^{18}$ and $R^{19}$ being the same or different;
  (i) a part of the sum of $X^9$, $X^{10}$ and $X^{11}$ is a functional group selected from the group consisting of a hydrocarbon group containing a 2-pyrrolidonyl group and an epoxy-containing group having 4 to 12 carbon atoms and the remainder of the sum of $X^9$, $X^{10}$ and $X^{11}$ is a group derived from said functional group by the reaction of said functional group with an active metal at a terminal of the active conjugated diene polymer chains, or (ii) a part of the sum of $X^9$, $X^{10}$ and $X^{11}$ is an alkoxyl group having 1 to 5 carbon atoms and the remainder of the sum of $X^9$, $X^{10}$ and $X^{11}$ is a single bond; and
  s is an integer of 1 to 18, and
(B) 95% to 5% by weight of conjugated diene rubber having a weight average molecular weight in the range of 1,000 to 3,000,000 which is a reaction product of an active conjugated diene polymer chain having an active metal at a terminal thereof with a compound selected from the group consisting of:
N-substituted cyclic amides,
N-substituted cyclic ureas,
N-substituted amino ketones,
aromatic isocyanates,
N,N,N',N'-tetramethylthiourea,
N,N-disubstituted aminoalkylmethacrylamides,
N-substituted aminoaldehydes,
N-substituted carbodiimides,
Schiff bases,
propylene oxide,
tetraglycidyl-1,3-bisaminomethylcyclohexane,
epoxidized polybutadiene,
vinyl compounds having a pyridyl group,
bis(triethoxysilylpropyl)-tetrasulfide,
bis(tributoxysilylpropyl)tetrasulfide,
γ-glydoxypropyltrimethoxysilane,
tetramethoxysilane,
tin tetrachloride,
silicon tetrachioride,
triphenylmonochlorotin,
triphenoxychlorosilane,
methyltriphenoxysilane, and
diphenoxydichlorosilane.

2. The conjugated diene rubber composition according to claim 1, wherein the polymer chain constituting the conjugated diene rubber (A) and the polymer chain constituting the conjugated diene rubber (B) comprise 50% to 100% by weight of conjugated diene monomer units and 50% to 0% by weight of aromatic vinyl monomer units.

3. The conjugated diene rubber composition according to claim 1, wherein the conjugated diene monomer units in the conjugated diene rubber (A) and the conjugated diene monomer units in the conjugated diene rubber (B) have a vinyl bond content of 5% to 95% by weight.

4. The conjugated diene rubber composition according to claim 1, wherein the polyorganosiloxane is represented by the general formula (1), and the functional group for $X^1$, $X^2$ and $X^4$ in the formula (1) is a hydrocarbon group containing a 2-pyrrolidonyl group represented by the following general formula (4);

General formula (4):

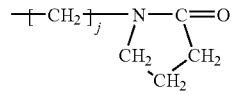

wherein j is an integer of 2 to 10.

5. The conjugated diene rubber composition according to claim 1, wherein the polyorganosiloxane is represented by the general formula (1), and the functional group for $X^1$, $X^2$ and $X^4$ in the formula (1) is a group having 4 to 12 carbon atoms and containing an epoxy group represented by the following general formula (5):

ZYE wherein Z is an alkylene group or an alkylarylene group, which have 1 to 10 carbon atoms, Y is a methylene group, a sulfur atom or an oxygen atom, and B is a group having 2 to 10 carbon atoms and containing an epoxy group.

6. The conjugated diene rubber composition according to claim 1, wherein the group comprising 2 to 20 alkylene glycol repeating units for $X^3$ in the formula (1) is a group represented by the following general formula (6):

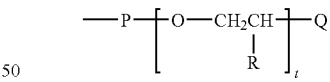

wherein t is an integer of 2 to 20, P is an alkylene group or an alkylarylene group, which have 2 to 10 carbon atoms, R is a hydrogen atom or a methyl group, Q is an alkoxyl group or an aryloxy group, which have 1 to 10 carbon atoms, provided that a part of Q may be a single bond.

7. The conjugated diene rubber composition according to claim 1, wherein the conjugated diene rubber (A) comprises 2 to 90% by weight, based on the conjugated diene rubber (A), of a conjugated diene rubber wherein at least four of the conjugated diene polymer chains in said rubber are bonded together through at least one polyorganosiloxane selected from those which are represented by the formulae (1), (2) and (3).

8. The conjugated diene rubber composition according to claim 1, which further comprises 5 to 150 parts by weight, based on 100 parts by weight of the total conjugated diene rubbers (A) and (B), of at least one filler selected from silica and carbon black.

9. The conjugated diene rubber composition according to claim 8, which comprises silica alone or both of silica and carbon black as the filler.

10. The conjugated diene rubber composition according to claim 1, which further comprises not larger than 900 parts by weight, based on 100 parts by weight of the total conjugated diene rubbers (A) and (B), of a polymer having a glass transition temperature in the range of −120° C. to 200° C. and a weight average molecular weight of 1,000 to 3,000,000.

11. A rubber vulcanizate which is obtained by crosslinking a conjugated diene rubber composition comprising:

(A) 5% to 95% by weight of a conjugated diene rubber having a weight average molecular weight in the range of 1,000 to 3,000,000 wherein at least three conjugated diene polymer chains in said rubber are bonded together through at least one polyorganosiloxane selected from those which are represented by the general formulae (1), (2) and (3), shown below:

General formula (1):

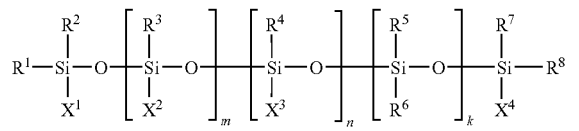

wherein
R$^1$ through R$^8$ represent an alkyl group having 1 to 6 carbon atoms or an aryl group having 6 to 12 carbon atoms, R$^1$ through R$^8$ being the same or different;

(i) a part of the sum of X$^1$ and X$^4$ is a functional group selected from the group consisting of a hydrocarbon group containing a 2-pyrrolidonyl group and an epoxy-containing group having 4 to 12 carbon atoms and the remainder of the sum of X$^1$ and X$^4$ is a group derived from said functional group by the reaction of said functional group with an active metal at a terminal of the active conjugated diene polymer chains, or (ii) a part of the sum of X$^1$ and X$^4$ is an alkoxyl group having 1 to 5 carbon atoms and the remainder of the sum of X$^1$ and X$^4$ is a single bond, or (iii) X$^1$ and X$^4$ are an alkyl group having 1 to 6 carbon atoms or an aryl group having 6 to 12 carbon atoms, X$^1$ and X$^4$ being the same or different;

(i) a part of X$^2$ is a functional group selected from the group consisting of a hydrocarbon group containing a 2-pyrrolidonyl group and an epoxy-containing group having 4 to 12 carbon and the remainder of X$^2$ is a group derived from said functional group by the reaction of said functional group with an active metal at a terminal of the active conjugated diene polymer chains, or (ii) a part of X$^2$ is an alkoxyl group having 1 to 5 carbon atoms and the remainder of X$^2$ is a single bond;

X$^3$ is a group comprising 2 to 20 alkylene glycol repeating units, provided that a part of may be a group derived from the group comprising 2 to 20 alkylene glycol repeating units; and m is an integer of 3 to 200, n is an integer of 0 to 200 and k is an integer of 0 to 200;

General formula (2):

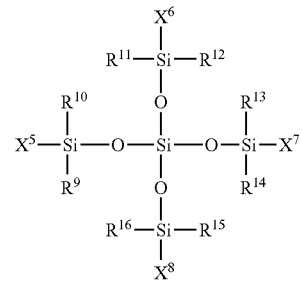

wherein
R$^9$ through R$^{16}$ represent an alkyl group having 1 to 6 carbon atoms or an aryl group having 6 to 12 carbon atoms, R$^9$ through R$^{16}$ being the same or different; and (i) a part of the sum of X$^5$ through X$^8$ is a functional group selected from the group consisting of a hydrocarbon group containing a 2-pyrrolidonyl group and an epoxy-containing group having 4 to 12 carbon atoms and the remainder of the sum of X$^5$ through X$^8$ is a group derived from said functional group by the reaction of said functional group with an active metal at a terminal of the active conjugated diene polymer chains, or (ii) a part of the sum of X$^5$ through X$^8$ is an alkoxyl group having 1 to 5 carbon atoms and the remainder of the sum of X$^5$ through X$^8$ is a single bond;

General formula (3):

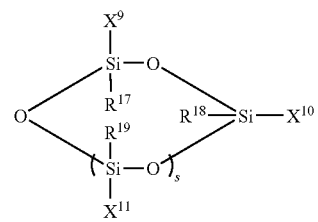

wherein
R$^{17}$, R$^{18}$ and R$^{19}$ represent an alkyl group having 1 to 6 carbon atoms or an aryl group having 6 to 12 carbon atoms, R$^{17}$, R$^{18}$ and R$^{19}$ being the same or different;

(i) a part of the sum of X$^9$, X$^{10}$ and X$^{11}$ is a functional group selected from the group consisting of a hydrocarbon group containing a 2-pyrrolidonyl group and an epoxy-containing group having 4 to 12 carbon atoms and the remainder of the sum of X$^9$, X$^{10}$ and X$^{11}$ is a group derived from said functional group by the reaction of said functional group with an active metal at a terminal of the active conjugated diene polymer chains, or (ii) a part of the sum of X$^9$, X$^{10}$ and X$^{11}$ is an alkoxyl group having 1 to 5 carbon atoms and the remainder of the sum of X$^9$, X$^{10}$ and X$^{11}$ is a single bond; and s is an integer of 1 to 18, and (B) 95% to 5% by weight of a conjugated diene rubber having a weight average molecular weight in the range of 1,000 to 3,000,000 which is a reaction product of an active conjugated diene polymer chain having an active metal at a terminal thereof with a compound selected from the group consisting of: N-substituted cyclic amides, N-substituted cyclic ureas, N-substituted amino ketones, aromatic isocyanates, N,N,N',N'-tetramethylthiourea, N,N-disubstituted aminoalkylmethacrylamides, N-substituted aminoaldehydes, N-substituted carbodiimides, Schiff bases, propylene oxide, tetraglycidyl-1,3-bisaminomethylcyclohexane, epoxidized polybutadiene, vinyl compounds having a pyridyl group, bis(triethoxysilylpropyl)tetrasulfide, bis(tributoxysilylpropyl)tetrasulfide, γ-glydoxypropyltrimethoxysilane, tetramethoxysilane, tin tetrachloride, silicon tetrachloride, triphenylmonochlorotin, triphenoxychlorosilane, methyltriphenoxysilane, and diphenoxydichlorosilane.

12. The rubber vulcanizate according to claim 11, which is a tire.

13. The conjugated diene rubber composition according to claim 1, wherein said conjugated diene polymer chains in said rubber (A) and said rubber (B) comprise 50 to 100% by weight of conjugated diene monomer and 50 to 0% by weight of aromatic vinyl monomer.

* * * * *